(12) United States Patent
Cote et al.

(10) Patent No.: US 11,678,926 B2
(45) Date of Patent: *Jun. 20, 2023

(54) TETHERED SYSTEM FOR CRYOGENIC TREATMENT

(71) Applicant: Channel Medsystems, Inc., Emeryville, CA (US)

(72) Inventors: Ulric E. Cote, Oakland, CA (US); William Malecki, Piedmont, CA (US); Scott Sylliaasen, Kensington, CA (US); David Beaulieu, El Cerrito, CA (US); Sarah Blood, Oakland, CA (US); Vincent Lopresti, San Francisco, CA (US); Paul Munro, San Jose, CA (US)

(73) Assignee: Channel Medsystems, Inc., Berkeley, CA (US)

( * ) Notice: Subject to any disclaimer, the term of this patent is extended or adjusted under 35 U.S.C. 154(b) by 377 days.

This patent is subject to a terminal disclaimer.

(21) Appl. No.: 16/666,145

(22) Filed: Oct. 28, 2019

(65) Prior Publication Data

US 2020/0078072 A1    Mar. 12, 2020

Related U.S. Application Data

(63) Continuation of application No. 15/605,630, filed on May 25, 2017, now Pat. No. 10,492,844.

(51) Int. Cl.
*A61B 18/02* (2006.01)
*A61B 90/98* (2016.01)
(Continued)

(52) U.S. Cl.
CPC .......... *A61B 18/0218* (2013.01); *A61B 18/02* (2013.01); *A61B 90/90* (2016.02);
(Continued)

(58) Field of Classification Search
CPC ..... A61B 18/0218; A61B 18/02; A61B 90/90; A61B 90/98; A61B 2018/00172;
(Continued)

(56) References Cited

U.S. PATENT DOCUMENTS 5,976,123 A * 11/1999 Baumgardner .... A61B 18/0218
606/13
6,017,337 A * 1/2000 Pira ........................ A61B 18/02
601/15
(Continued)

FOREIGN PATENT DOCUMENTS

EP         0987989        3/2000
WO    WO 2004/000092    12/2003
(Continued)

*Primary Examiner* — Michael F Peffley
*Assistant Examiner* — Amanda L Zink
(74) *Attorney, Agent, or Firm* — Levine Bagade Han LLP

(57) ABSTRACT

A tethered system for cryogenic treatment is disclosed in which a hand piece having an elongate probe with a distal tip and a flexible length, at least one infusion lumen positioned through or along the elongate probe, and a liner may be tethered to a base station having a reservoir of a cryoablative fluid via a connection having an elongate flexible body. The connection defines at least one fluid lumen for delivery of the cryoablative fluid from the reservoir and to the infusion lumen within the hand piece.

20 Claims, 17 Drawing Sheets

(51) Int. Cl.
*A61B 90/90* (2016.01)
*A61B 18/00* (2006.01)
*A61B 90/00* (2016.01)

(52) U.S. Cl.
CPC ...... *A61B 90/98* (2016.02); *A61B 2018/0022* (2013.01); *A61B 2018/00172* (2013.01); *A61B 2018/00559* (2013.01); *A61B 2018/00577* (2013.01); *A61B 2018/00642* (2013.01); *A61B 2018/00791* (2013.01); *A61B 2018/00898* (2013.01); *A61B 2018/0212* (2013.01); *A61B 2018/0262* (2013.01); *A61B 2090/064* (2016.02)

(58) Field of Classification Search
CPC .. A61B 2018/0022; A61B 2018/00559; A61B 2018/00577; A61B 2018/00642; A61B 2018/00791; A61B 2018/00898; A61B 2018/0212; A61B 2018/0262; A61B 2090/064; A61B 2017/0046; A61B 2018/00744
See application file for complete search history.

(56) References Cited

U.S. PATENT DOCUMENTS

| | | | |
|---|---|---|---|
| 6,159,160 A | 12/2000 | Hsei et al. | |
| 6,235,019 B1 | 5/2001 | Lehmann et al. | |
| 6,270,476 B1 | 8/2001 | Santoianni et al. | |
| 6,270,493 B1 | 8/2001 | Lalonde et al. | |
| 6,280,439 B1 | 8/2001 | Martin et al. | |
| 6,283,959 B1 | 9/2001 | Lalonde et al. | |
| 6,554,780 B1 | 4/2003 | Sampson et al. | |
| 6,569,158 B1 | 5/2003 | Abboud et al. | |
| 6,743,184 B2 | 6/2004 | Sampson et al. | |
| 6,872,183 B2 | 3/2005 | Sampson et al. | |
| 7,063,670 B2 | 6/2006 | Sampson et al. | |
| 7,101,367 B2 | 9/2006 | Xiao et al. | |
| 7,381,208 B2 | 6/2008 | van der Walt et al. | |
| 7,500,973 B2 | 3/2009 | Vancelette et al. | |
| 8,206,345 B2 | 6/2012 | Abboud et al. | |
| 8,225,643 B2 | 7/2012 | Abboud et al. | |
| 8,382,747 B2 | 2/2013 | Abboud et al. | |
| 9,027,389 B2 | 5/2015 | Abboud et al. | |
| 9,445,860 B2 | 9/2016 | Burnett et al. | |
| 9,522,030 B2 | 12/2016 | Harmouche et al. | |
| 10,492,844 B2* | 12/2019 | Cote | A61B 18/0218 |
| 2002/0143323 A1* | 10/2002 | Johnston | A61B 34/35 606/21 |
| 2004/0243202 A1 | 12/2004 | Lennox | |
| 2005/0261753 A1 | 11/2005 | Littrup et al. | |
| 2006/0122589 A1 | 6/2006 | Abboud et al. | |
| 2008/0009747 A1* | 1/2008 | Saadat | A61B 1/04 600/471 |
| 2012/0197245 A1 | 8/2012 | Burnett et al. | |
| 2013/0104993 A1 | 5/2013 | Groves et al. | |
| 2013/0190745 A1* | 7/2013 | Fourkas | A61B 18/02 606/25 |
| 2013/0296837 A1* | 11/2013 | Burnett | A61B 5/4836 606/21 |
| 2015/0080869 A1* | 3/2015 | Burnett | A61B 18/02 606/21 |
| 2015/0088113 A1* | 3/2015 | Clark | A61B 18/02 606/21 |
| 2015/0021658 A1 | 8/2015 | Duong et al. | |
| 2015/0289920 A1* | 10/2015 | Burnett | A61B 18/02 606/24 |
| 2016/0138006 A1* | 5/2016 | Canady | H05H 1/46 606/34 |
| 2017/0007310 A1* | 1/2017 | Rajagopalan | A61B 18/1815 |
| 2017/0007324 A1 | 1/2017 | Kadamus et al. | |
| 2017/0112559 A1* | 4/2017 | Sylliaasen | A61J 1/1475 |
| 2017/0333122 A1* | 11/2017 | Rajagopalan | A61B 18/1492 |
| 2017/0348049 A1* | 12/2017 | Vrba | A61B 18/1492 |
| 2018/0071006 A1* | 3/2018 | Burnett | A61B 18/02 |
| 2018/0310950 A1* | 11/2018 | Yee | A61B 18/0218 |
| 2018/0338787 A1 | 11/2018 | Cote et al. | |
| 2019/0274746 A1* | 9/2019 | Toth | A61K 31/045 |

FOREIGN PATENT DOCUMENTS

| | | |
|---|---|---|
| WO | WO 2012/106260 | 8/2012 |
| WO | WO 2013/067421 | 5/2013 |
| WO | WO 2018/217412 | 11/2018 |

* cited by examiner

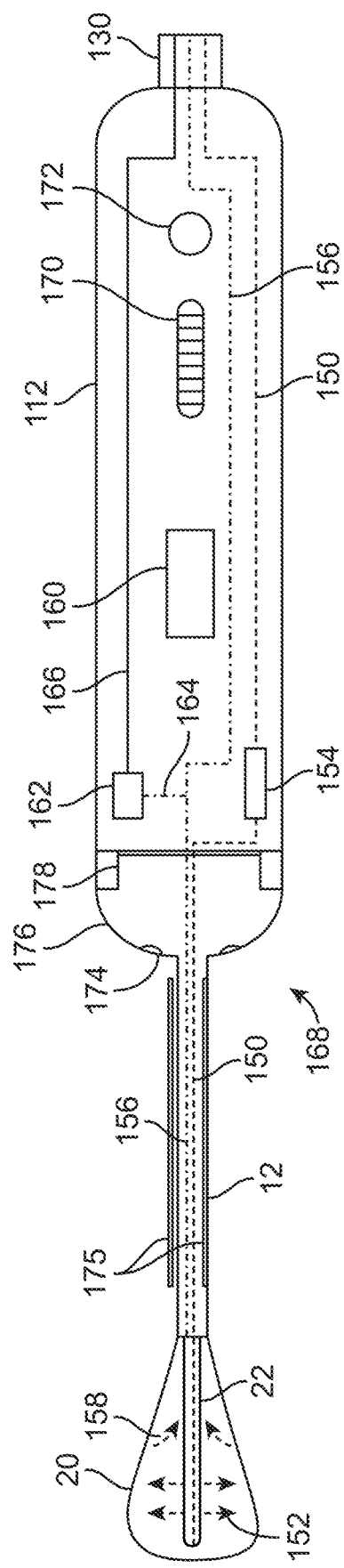
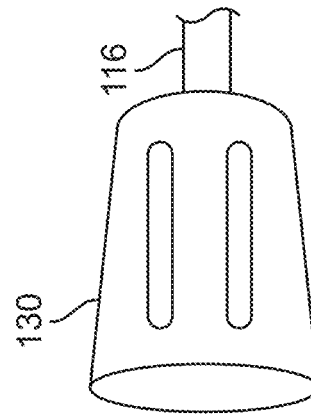
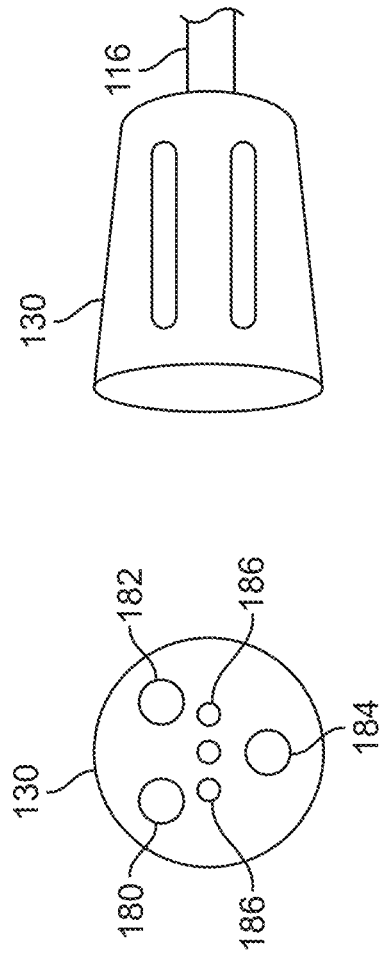
FIG. 6
FIG. 7A
FIG. 7B

TETHERED SYSTEM FOR CRYOGENIC TREATMENT

CROSS-REFERENCE TO RELATED APPLICATIONS

This application is a continuation of U.S. patent application Ser. No. 15/605,630 filed May 25, 2017 (now U.S. Pat. No. 10,492,844), the content of which is incorporated herein by reference in its entirety.

FIELD OF THE INVENTION

The present invention relates to medical devices. In particular, the present invention relates to methods and apparatus for the cryoablative treatment of tissue regions using a hand piece and base tethered to one another.

BACKGROUND OF THE INVENTION

While the delivery of energy via radiofrequency ablation is used in several arenas, radiofrequency ablation has several major downsides, including incomplete ablation, frequent lack of visualization during catheter insertion, potential for overlap during treatment (with some areas receiving twice as much energy as other areas), charring of tissues and requirements for frequent debridement, frequent requirements for additional doses of energy after debridement, and potential perforation of the body cavity or lumen due to the rigidity of the RF electrodes.

Other treatments involve the delivery of a cryogenic agent for ablating the contacted tissue within the body of a subject. Yet such systems require a connection to a reservoir of a cryoablative fluid for delivery of the fluid as well as withdrawal of any exhausted fluid from the patient body.

The current state of the art would benefit from minimally invasive devices and methods which deliver thermal energy to a desired area or extract energy from a desired area using a system which is ergonomic and facilitates ease of use by the practitioner.

SUMMARY OF THE INVENTION

A cryoablation treatment assembly may include a base station having a reservoir housing and electronics which may be detached entirely from a hand piece having a sheath and liner assembly such that the treatment assembly is formed as a two-part or multi-component system which may be tethered or otherwise connected to one another. The hand piece may be separated from the base station which incorporates the reservoir and controller. A flexible connection may attach the hand piece with the base station where the hand piece may either be permanently coupled to the base station via the connection or where the hand piece may be detachable from the connection and/or from the base station.

One variation of a treatment system may generally comprise a hand piece having an elongate probe with a distal tip and a flexible length, at least one infusion lumen positioned through or along the elongate probe, and a liner expandably enclosing the probe such that a cryoablative fluid introduced through one or more unobstructed openings along the infusion lumen is sprayed into contact with an interior surface of the liner and coats the interior surface. The system may also include a base station having a reservoir of the cryoablative fluid and a connection having an elongate flexible body coupling the hand piece and the base station, wherein the connection defines at least one fluid lumen for delivery of the cryoablative fluid from the reservoir and to the infusion lumen within the hand piece.

One variation of a method for treating tissue may generally comprise securing a reservoir assembly within a receiving channel of a base station, and positioning a hand piece in proximity to a tissue region of interest, wherein the hand piece has an elongate probe with a distal tip and a flexible length, at least one infusion lumen positioned through or along the elongate probe, and a liner expandably enclosing the probe such that a cryoablative fluid introduced through one or more unobstructed openings along the infusion lumen is sprayed into contact with an interior surface of the liner and coats the interior surface. The method may also include infusing the cryoablative fluid from the reservoir assembly through a connection having an elongate flexible body and in fluid communication with the infusion lumen within the hand piece.

In controlling or modulating the flow of the cryoablative agent, the inflow reservoir or canister valve which is fluidly coupled with the reservoir or canister may be utilized. Such a valve may generally comprising a valve body, a reservoir interface extending from the valve body and configured for fluidly coupling with the reservoir or canister containing the cryoablative agent, a modulation control interface defined along the body and configured for fluidly coupling to a modulation control interface, a valve stem seated within a valve stem channel defined within the valve body, an inflow lumen defined through the valve body and extending between the reservoir interface and the modulation control interface, where the valve stem is movable between a first position which obstructs the inflow lumen and a second position which opens the inflow lumen, a venting lumen defined through the valve body and extending between the reservoir interface and a vent opening, and a vent piston which is movable between a first position which obstructs the venting lumen and a second position which opens the venting lumen. Alternatively, the valve stem may be configured to include three positions including a first position which obstructs the inflow lumen, a second position which opens the inflow lumen, and a third optional position which opens the venting lumen.

To facilitate the liner expanding and conforming readily against the tissue walls of the uterus, the liner may be inflated with a gas or liquid. Once the elongate shaft has been introduced through the cervix and into the uterus, the distal opening of the shaft may be positioned distal to the internal os and the liner may be deployed either from within the shaft or from an external sheath. The liner may be deployed and allowed to unfurl or unwrap within the uterus. The cooling probe may be introduced through the shaft and into the liner interior. As the cryoablative agent (e.g., cryoablative fluid) is introduced into and distributed throughout the liner interior, the exhaust catheter may also define one or more openings to allow for the cryoablative fluid to vent or exhaust from the interior of the liner.

A coolant reservoir, e.g., nitrous oxide canister, may be fluidly coupled to the handle and/or elongate shaft via a coolant valve which may be optionally controlled by the microcontroller. The coolant reservoir may be in fluid communication with the cooling probe assembly and with the interior of the balloon. Additionally, an exhaust lumen in communication with the elongate probe and having a back pressure valve may also include a pressure sensor where one or both of the back pressure sensor and/or valve may also be in communication with the microcontroller.

Yet another variation of the treatment assembly may incorporate a housing having a handle and a reservoir housing extending from and attached directly to the handle. The sheath having the liner may extend from the housing while an actuator may be located, for instance, along the handle to enable the operator to initiate the cryoablative treatment. A reservoir or canister fully containing the cryoablative fluid may be inserted and retained within the reservoir housing. The reservoir housing and/or the handle may further incorporate a reservoir engagement control which may be actuated, e.g., by rotating the control relative to the handle, to initially open fluid communication with the reservoir or canister to charge the system for treatment.

In an alternative variation, the reservoir housing and the electronics may be detached entirely from the sheath and liner assembly such that the treatment assembly is formed as a two-part or multi-component system which may be tethered or otherwise connected to one another. Rather than incorporating the reservoir housing and controller, the hand piece may be separated from a base station which incorporates the reservoir and controller. A flexible connection may attach the hand piece with the base station where the hand piece may either be permanently coupled to the base station via the connection or where the hand piece may be detachable from the connection and/or from the base station.

Because the treatment system is separated into at least two components which are in communication with one another, the system may provide an ergonomic hand piece which is relatively light yet still provides efficient treatment to the patient while remaining attached to its base station via the flexible connection. With the base station separated and housing the reservoir and multiple electronic and actuation components, the hand piece may be easily handled by the practitioner during treatment relative to the base station and the patient body.

The hand piece may optionally incorporate a display, e.g., LCD display, which shows various treatment parameters or indicators of the assembly. A control, e.g., thumbwheel, slide, etc., may also be incorporated for controlling functions such as positioning of the sheath and/or probe or other function. One or more actuators, e.g., button, switch, etc., may be incorporated as well for controlling functions such as infusing the cryoablative fluid into the liner or exhausting the fluid from the liner.

Other mechanisms such as a potentiometer, e.g., linear potentiometer, may be incorporated for detecting and/or monitoring the position of the sheath relative to the hand piece housing. A pressure sensor may also be incorporated for detecting and/or monitoring the pressure within the liner prior to, during, and/or after a treatment. Additionally, an inflow control, e.g., inflow solenoid, may be incorporated into the hand piece for controlling the inflow of the cryoablative fluid into the hand piece from the base station.

While the hand piece may be detachable from the base station and/or connection, an infusion attachment including, e.g., sheath, liner, and cooling probe, may also be removable and/or replaceable from the rest of the hand piece allowing for the replacement of the infusion attachment while reusing the hand piece. The hand piece may be maintained at a treatment location for sterilization while the infusion attachment may be disposed, refurbished, or repurposed on-site or at another location.

The connection may be coupled to the hand piece via a releasable connector, e.g., quick-connect mechanism, and it may be coupled to the base station also via a second releasable connector, e.g., quick-connect mechanism. The connection may enable the connection between the hand piece and base station to allow for the passage of various fluids and signals such as the cryoablation fluid, high pressure gas, electrical signals, pneumatic signals, etc. while remaining flexible enough so that the hand piece may be moved and adjusted relative to the patient independently of the base station which may remain in a stationary position relative to the patient.

The base station has a housing which may include a display, e.g., LCD touchscreen, etc., for enabling interaction with or the display of parameters, messages, or warnings to the practitioner. A programmable microcontroller may be integrated within the base station and is in electrical communication with the hand piece either through the connection or wirelessly to control the treatment parameters as well as to receive and process signals from the hand piece such as pressure readings, sheath positioning, etc. or any number of other signals. The microcontroller may also control the various parameters within the base station as well.

The base station may also incorporate a pump which may be fluidly coupled to the hand piece and used to draw the spent exhaust from the interior of the liner, through the hand piece and connection, and then through the base station to, e.g., an exhaust collection assembly. A pneumatics controller, which may also include a pump, may be incorporated into the base station and may be in fluid communication with the liner for controlling the infusion or withdrawal of air within the liner, e.g., when monitoring the liner for leaks or for initially expanding the liner within the patient body. At least one actuator, e.g., button, may also be integrated for initiating treatment steps or facilitating control of the base station during treatment. A reservoir assembly may also be included within the base station but may be removable from the base station.

BRIEF DESCRIPTION OF THE DRAWINGS

FIG. 6 shows a schematic view of one variation of the hand piece where an infusion attachment may be removably coupled to a distal end of the housing of the hand piece via a coupling mechanism.

FIGS. 7A and 7B show end and side views, respectively, of the connector for the hand piece.

DETAILED DESCRIPTION OF THE INVENTION

Figure 1A:
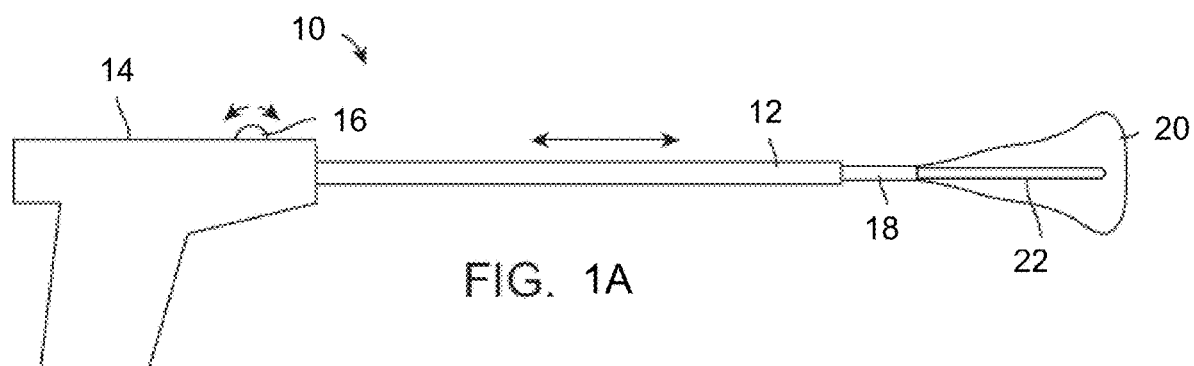
FIG. 1A shows a side view of an integrated treatment assembly.

The cooling probe 22 as well as the balloon assembly may be variously configured, for instance, in an integrated treatment assembly 10 as shown in the side view of FIG. 1A. In this variation, the assembly 10 may integrate the elongate shaft 18 having the liner or balloon 20 extending therefrom with the cooling probe 22 positioned translatably within the shaft 18 and liner 20. A separate translatable sheath 12 may be positioned over the elongate shaft 18 and both the elongate shaft 18 and sheath 12 may be attached to a handle assembly 14. The handle assembly 14 may further comprise an actuator 16 for controlling a translation of the sheath 12 for liner 20 delivery and deployment.

Figure 1B:
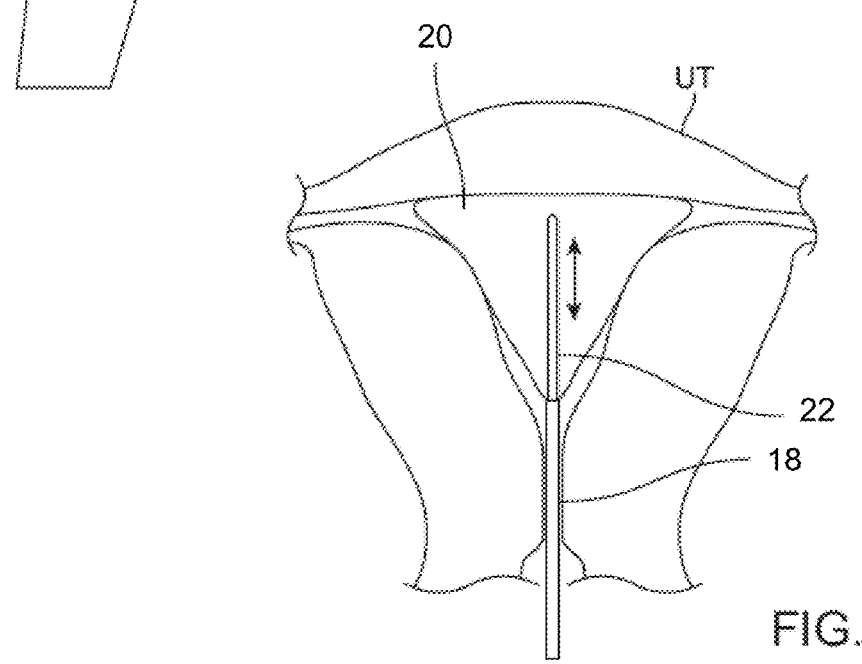
FIG. 1B shows an example of the assembly advanced through the cervix and into the uterus where the sheath may be retracted via the handle assembly to deploy the balloon.

With the sheath 12 positioned over the elongate shaft 18 and liner 20, the assembly 10 may be advanced through the cervix and into the uterus UT where the sheath 12 may be retracted via the handle assembly 14 to deploy the liner 20, as shown in FIG. 1B. As described above, once the liner 20 is initially deployed from the sheath 12, it may be expanded by an initial burst of a gas, e.g., air, carbon dioxide, etc., or by the cryoablative fluid. In particular, the tapered portions of the liner 20 may be expanded to ensure contact with the uterine cornu. The handle assembly 14 may also be used to actuate and control a longitudinal position of the cooling probe 22 relative to the elongate shaft 18 and liner 20 as indicated by the arrows.

Figure 1C:
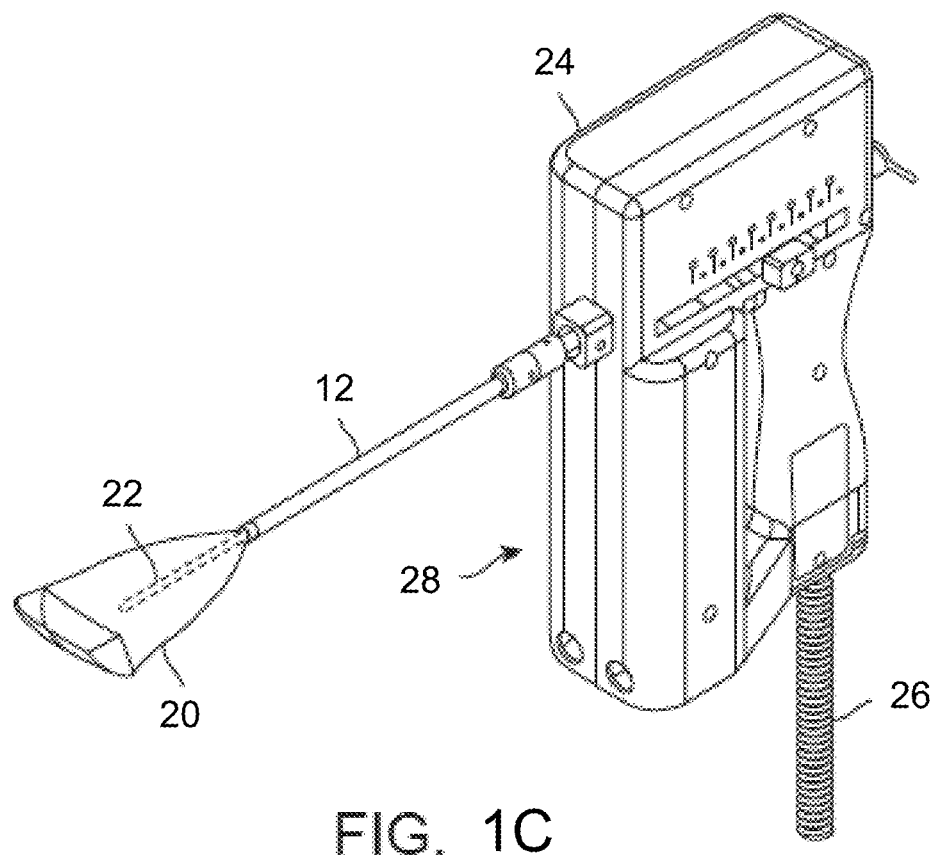
FIG. 1C shows a perspective view of a cryoablation assembly having a handle assembly which may integrate the electronics and pump assembly within the handle itself.

In another variation of the treatment assembly, FIG. 1C shows a perspective view of a cryoablation assembly having a handle assembly 24 which may integrate the electronics and pump assembly 28 within the handle itself. An exhaust tube 26 may also be seen attached to the handle assembly 24 for evacuating exhausted or excess cryoablative fluid or gas from the liner 20. Any of the cryoablative fluids or gases described herein may be utilized, e.g., compressed liquid-to-gas phase change of a compressed gas such as nitrous oxide ($N_2O$), carbon dioxide ($CO_2$), Argon, etc. The cooling probe 22 may be seen extending from sheath 12 while surrounded or enclosed by the liner or balloon 20. Hence, the handle assembly 24 with coupled cooling probe 22 and liner 20 may provide for a single device which may provide for pre-treatment puff-up or inflation of the liner 20, active cryoablation treatment, and/or post-treatment thaw cycles.

The handle assembly 24 may also optionally incorporate a display for providing any number of indicators and/or alerts to the user. For instance, an LCD display may be provided on the handle assembly 24 (or to a separate control unit connected to the handle assembly 24) where the display counts down the treatment time in seconds as the ablation is occurring. The display may also be used to provide measured pressure or temperature readings as well as any number of other indicators, symbols, or text, etc., for alerts, instructions, or other indications. Moreover, the display may be configured to have multiple color-coded outputs, e.g., green, yellow, and red. When the assembly is working through the ideal use case, the LED may be displayed as a solid green color. When the device requires user input (e.g. when paused and needing the user to press the button to re-start treatment) the LED may flash or display yellow. Additionally, when the device has faulted and treatment is stopped, the LED may flash or display a solid red color.

Figure 1D:
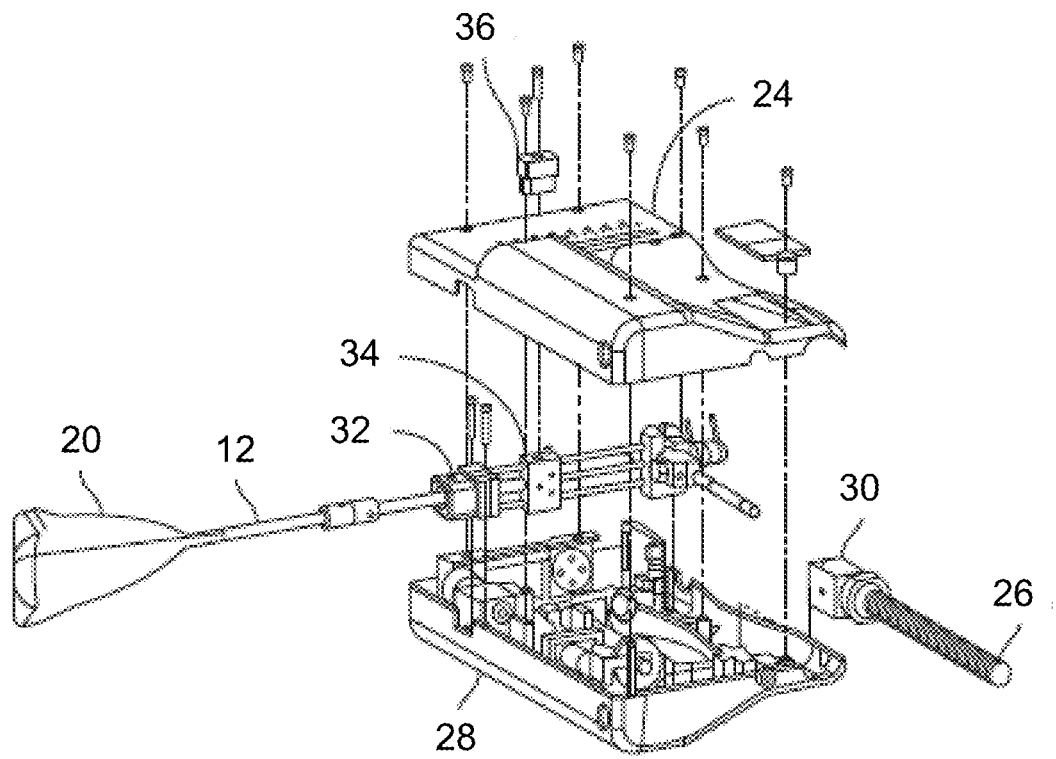
FIG. 1D shows the handle assembly in a perspective exploded view illustrating some of the components which may be integrated within the handle.

FIG. 1D shows the handle assembly 24 in a perspective exploded view to illustrate some of the components which may be integrated within the handle 24. As shown, the liner 20 and sheath 12 may be coupled to a sheath bearing assembly 32 and slider base block assembly 34 for controlling the amount of exposed treatment length along the cooling probe 22 (and as described in further detail below). An actuatable sheath control 36 may be attached to the slider base block assembly 34 for manually controlling the treatment length of the cooling probe 22 as well. Along with the electronics and pump assembly 28 (which may optionally incorporate a programmable processor or controller in electrical communication with any of the mechanisms within the handle 24), an exhaust valve 30 (e.g., actuated via a solenoid) may be coupled to the exhaust line 26 for controlling not only the outflow of the exhausted cryoablation fluid or gas but also for creating or increasing a backpressure during treatment, as described in further detail below.

Figure 1E:
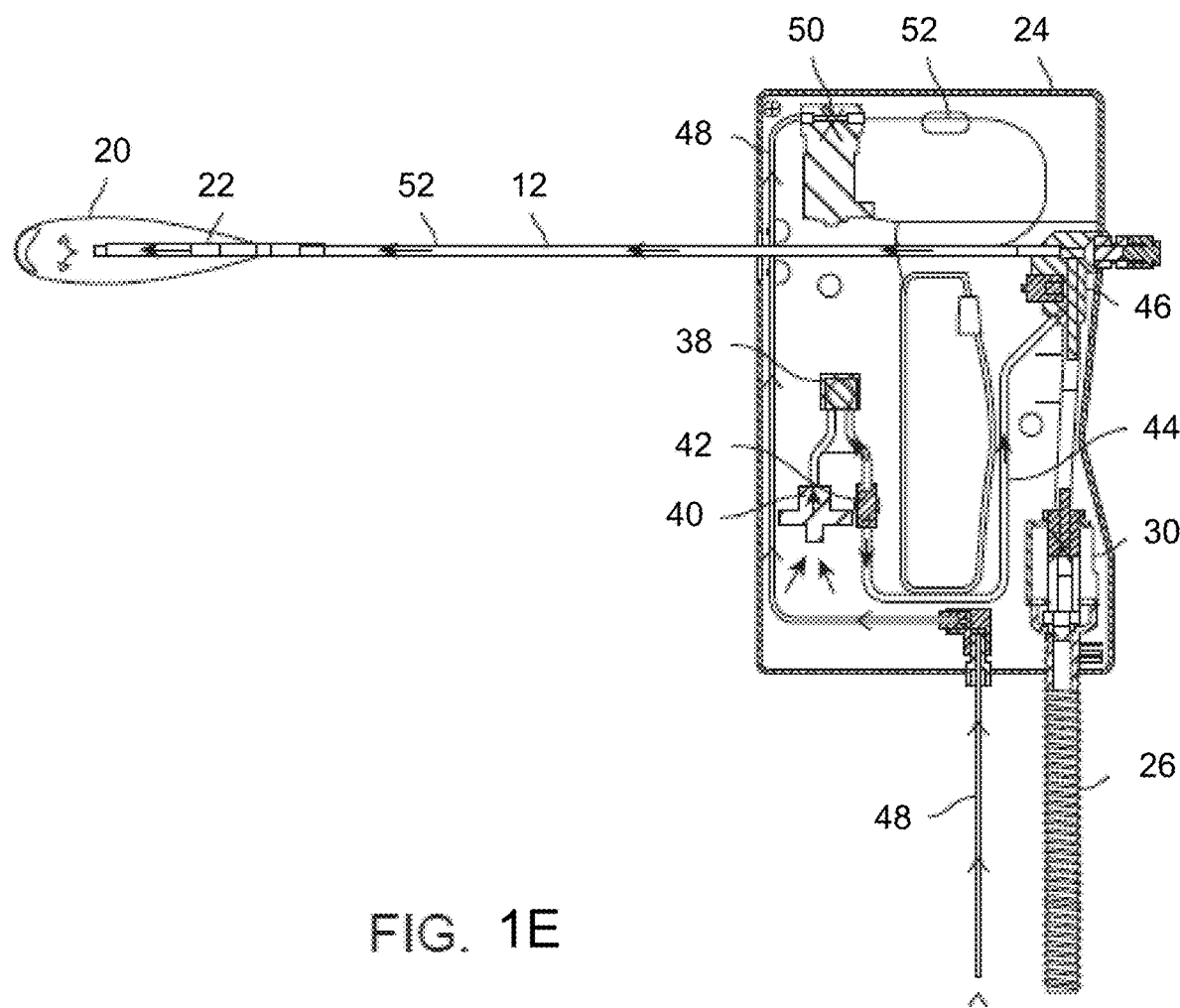
FIG. 1E shows an example of the system operation during a pre-treatment puff up process.
Figure 1F:
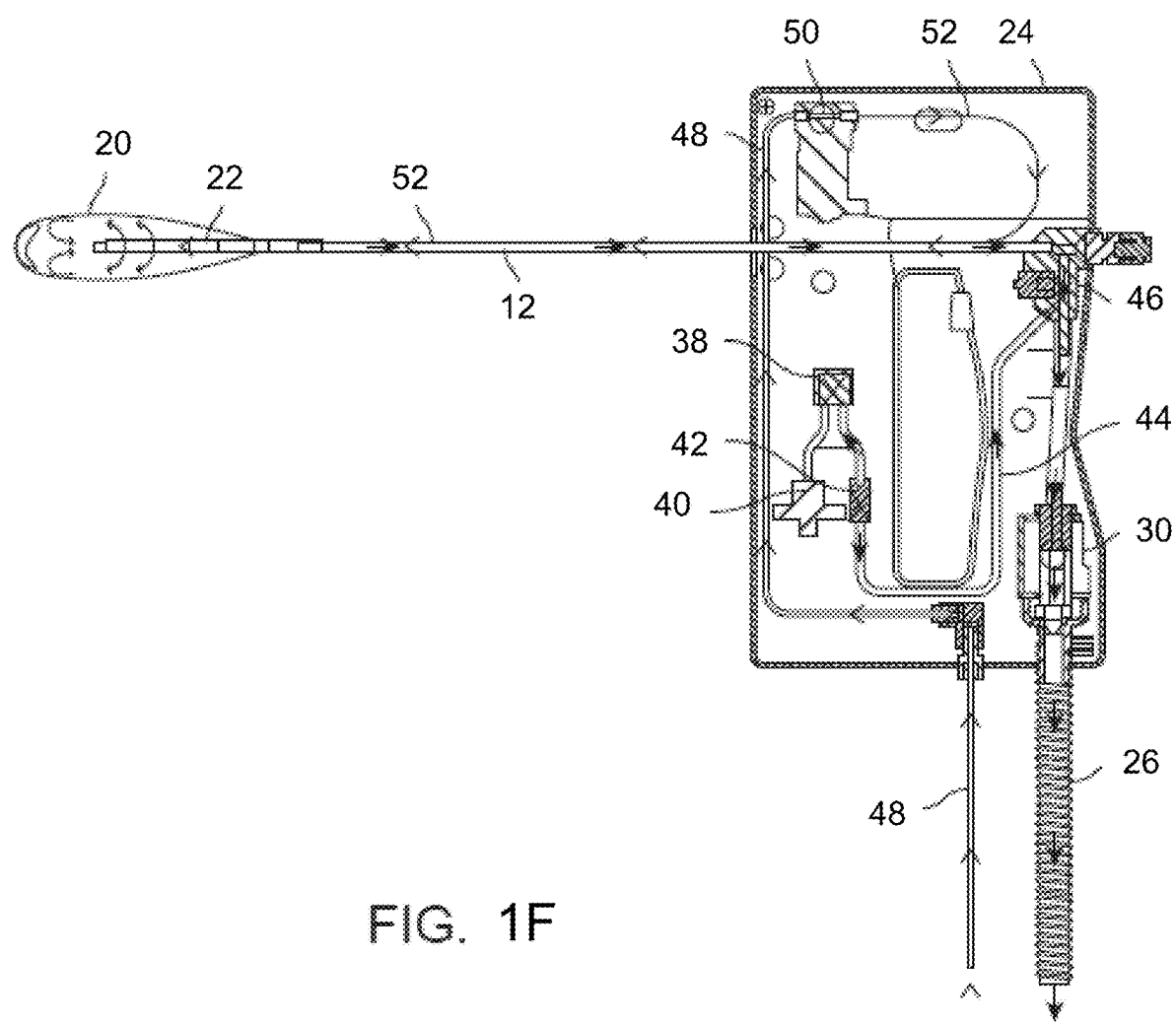
FIG. 1F shows an example of the system operation during a treatment process.
Figure 1G:
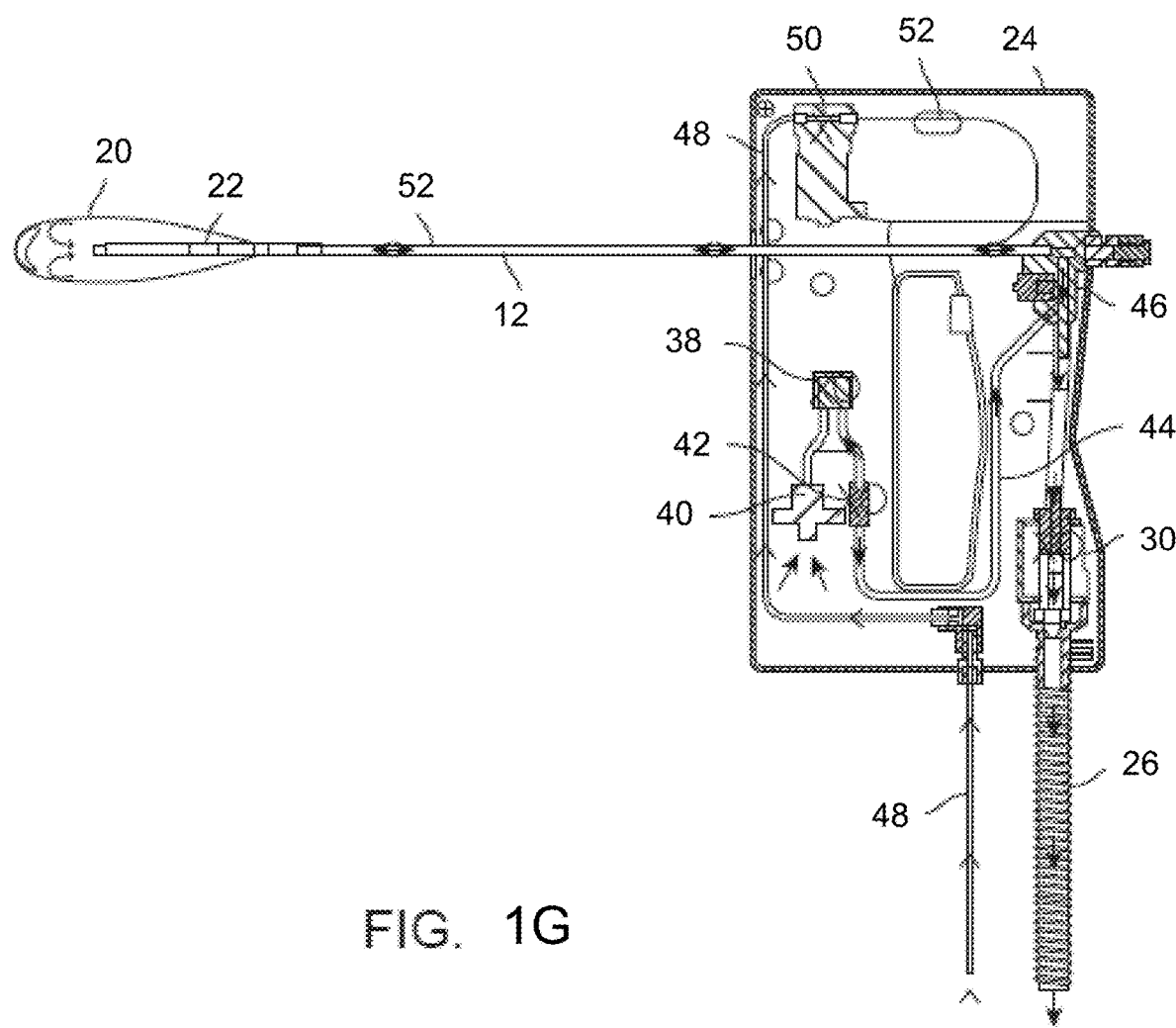
FIG. 1G shows an example of the system operation during a thawing and venting process.

In one example of how the handle assembly 24 may provide for treatment, FIGS. 1E to 1G illustrate schematic side views of how the components may be integrated and utilized with one another. As described herein, once the sheath 12 and/or liner 20 has been advanced and initially introduced into the uterus, the liner 20 may be expanded or inflated in a pre-treatment puff up to expand the liner 20 into contact against the uterine tissue surfaces in preparation for a cryoablation treatment. As illustrated in the side view of FIG. 1E, a pump 38 integrated within the handle assembly 24 may be actuated and a valve 42 (e.g., actuatable or passive) fluidly coupled to the pump 38 may be opened (as indicated schematically by an "O" over both the pump 38 and valve 42) such that ambient air may be drawn in through, e.g., an air filter 40 integrated along the handle 24, and passed through an air line 44 within the handle and to an exhaust block 46. The exhaust block 46 and air line 44 may be fluidly coupled to the tubular exhaust channel which extends from the handle 24 which is further attached to the cooling probe 22. As the air is introduced into the interior of the liner 20 (indicated by the arrows), the liner 20 may be expanded into contact against the surrounding uterine tissue surface.

A cryoablative fluid line 48 also extending into and integrated within the handle assembly 24 may be fluidly coupled to an actuatable valve 50, e.g., actuated via a solenoid, which may be manually closed or automatically closed (as indicated schematically by an "X" over the valve 50) by a controller to prevent the introduction of the cryoablative fluid or gas into the liner 20 during the pre-treatment liner expansion. An infusion line 52 may be fluidly coupled to the valve 50 and may also be coupled along the length of the sheath 12 and probe 22, as described in further detail below. The exhaust valve 30 coupled to the exhaust line 26 may also be closed (as indicated schematically by an "X" over the valve 30) manually or automatically by the controller to prevent the escape of the air from the exhaust block 46.

During this initial liner expansion, the liner 20 may be expanded in a gradual and controlled manner to minimize any pain which may be experienced by the patient in opening the uterine cavity. Hence, the liner 20 may be expanded gradually by metering in small amounts of air. Optionally, the pump 38 may be programmed and controlled by a processor or microcontroller to expand the liner 20 according to an algorithm (e.g., e.g. ramp-up pressure quickly to 10 mm Hg and then slow-down the ramp-up as the pressure increases to 85 mm Hg) which may be stopped or paused by the user. Moreover, the liner 20 may be expanded to a volume which is just sufficient to take up space within the uterine cavity. After the initial increase in pressure, the pressure within the liner 20 may be optionally increased in bursts or pulses. Moreover, visualization (e.g., via a hysteroscope or abdominal ultrasound) may be optionally used during the controlled gradual expansion to determine when the uterine cavity is fully open and requires no further pressurization. In yet another variation, the liner 20 may be cyclically inflated and deflated to fully expand the liner. The inflations and deflations may be partial or full depending upon the desired expansion.

In yet another alternative variation, the system could also use an amount of air pumped into the liner 20 as a mechanism for detecting whether the device is in a false passage of the body rather than the uterine cavity to be treated. The system could use the amount of time that the pump 38 is on to track how much air has been pushed into the liner 20. If the pump 38 fails to reach certain pressure levels within a predetermined period of time, then the controller may indicate that the device is positioned within a false passage. There could also be a limit to the amount of air allowed to be pushed into the liner 20 as a way to detect whether the probe 22 has been pushed, e.g., out into the peritoneal cavity. If too much air is pushed into the liner 20 (e.g., the volume of air tracked by the controller exceeds a predetermined level) before reaching certain pressures, then the controller may indicate the presence of a leak or that the liner 20 is not fully constrained by the uterine cavity. The liner 20 may also incorporate a release feature which is configured to rupture if the liner 20 is not constrained such that if the system attempts to pump up the liner 20 to treatment pressure (e.g., 140 mmHg), the release feature will rupture before reaching that pressure.

Once the liner 20 has been expanded sufficiently into contact against the uterine tissue surface, the cryoablation treatment may be initiated. As shown in the side view of FIG. 1F, the air pump 38 may be turned off and the valve 42 may be closed (as indicated schematically by an "X" over the pump 38 and valve 42) to prevent any further infusion of air into the liner 20. With the cryoablative fluid or gas pressurized within the line 48, valve 50 may be opened (as indicated schematically by an "O" over the valve 50) to allow for the flow of the cryoablative fluid or gas to flow through the infusion line 52 coupled to the valve 50. Infusion line 52 may be routed through or along the sheath 12 and along the probe 22 where it may introduce the cryoablative fluid or gas within the interior of liner 20 for infusion against the liner 20 contacted against the surrounding tissue surface.

During treatment or afterwards, the exhaust valve 30 may also be opened (as indicated schematically by an "O" over the valve 30) to allow for the discharged fluid or gas to exit or be drawn from the liner interior and proximally through the cooling probe 22, such as through the distal tip opening. The fluid or gas may exit from the liner 20 due to a pressure differential between the liner interior and the exhaust exit and/or the fluid or gas may be actively drawn out from the liner interior, as described in further detail herein. The spent fluid or gas may then be withdrawn proximally through the probe 22 and through the lumen surrounded by the sheath 12, exhaust block 46, and the exhaust tube 26 where the spent fluid or gas may be vented. With the treatment fluid or gas thus introduced through infusion line 52 within the liner 20 and then withdrawn, the cryoablative treatment may be applied uninterrupted.

Once a treatment has been completed, the tissue of the uterine cavity may be permitted to thaw. During this process, the cryoablative fluid delivery is halted through the infusion line 52 by closing the valve 50 (as indicated schematically by an "X" over the valve 50) while continuing to exhaust for any remaining cryoablative fluid or gas remaining within the liner 20 through probe 22, through the lumen surrounded by sheath 12, and exhaust line 26, as shown in FIG. 1G. Optionally, the pump 38 and valve 42 may be cycled on and off and the exhaust valve 30 may also be cycled on and off to push ambient air into the liner 20 to facilitate the thawing of the liner 20 to the uterine cavity. Optionally, warmed or room temperature air or fluid (e.g., saline) may also be pumped into the liner 20 to further facilitate thawing of the tissue region.

As the spent cryoablative fluid or gas is removed from the liner 20, a drip prevention system may be optionally incorporated into the handle. For instance, a passive system incorporating a vented trap may be integrated into the handle which allows exhaust gas to escape but captures any vented liquid. The exhaust line 26 may be elongated to allow for any vented liquid to evaporate or the exhaust line 26 may be convoluted to increase the surface area of the exhaust gas tube to promote evaporation.

Alternatively, an active system may be integrated into the handle or coupled to the handle 24 where a heat sink may be connected to a temperature sensor and electrical circuit which is controlled by a processor or microcontroller. The heat sink may promote heat transfer and causes any liquid exhaust to evaporate. When the temperature of the heat sink reaches the boiling temperature of, e.g., nitrous oxide (around −86° C.), the handle may be configured to slow or stop the delivery of the cryoablative fluid or gas to the uterine cavity.

The pre-treatment infusion of air as well as the methods for treatment and thawing may be utilized with any of the liner, probe, or apparatus variations described herein. Moreover, the pre-treatment, treatment, or post-treatment procedures may be utilized altogether in a single procedure or different aspects of such procedures may be used in varying combinations depending upon the desired results.

Additionally and/or optionally, the handle 24 may incorporate an orientation sensor to facilitate maintaining the handle 24 in a desirable orientation for treatment. One variation may incorporate a ball having a specific weight covering the exhaust line 26 such that when the handle 24 is held in the desirable upright orientation, the treatment may proceed uninterrupted. However, if the handle 24 moved out of its desired orientation, the ball may be configured to roll out of position and trigger a visual and/or auditory alarm to alert the user. In another variation, an electronic gyroscopic sensor may be used to maintain the handle 24 in the desired orientation for treatment.

Figure 2A:
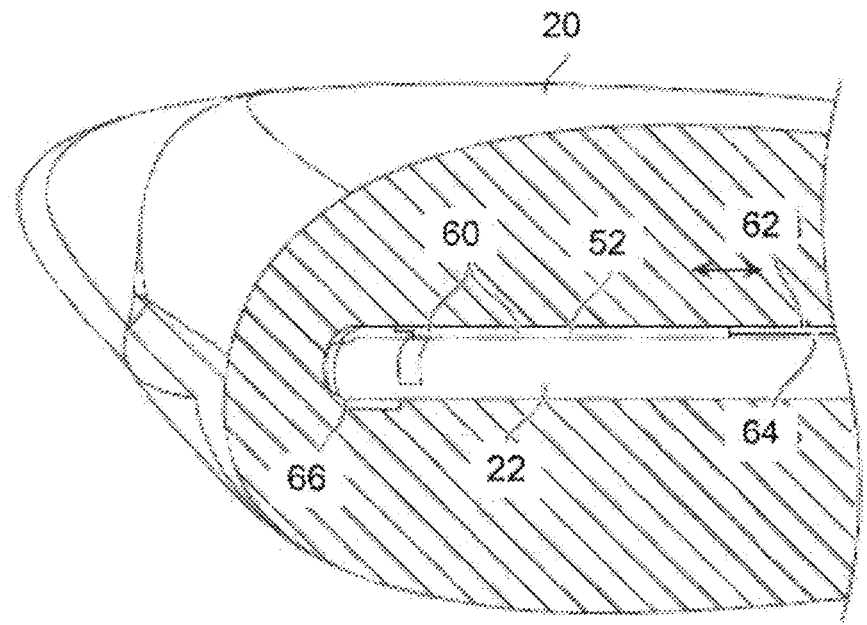
FIGS. 2A and 2B show cross-sectional side views of yet another variation of a cooling probe which utilizes a single infusion line in combination with a translatable delivery line.
Figure 2B:
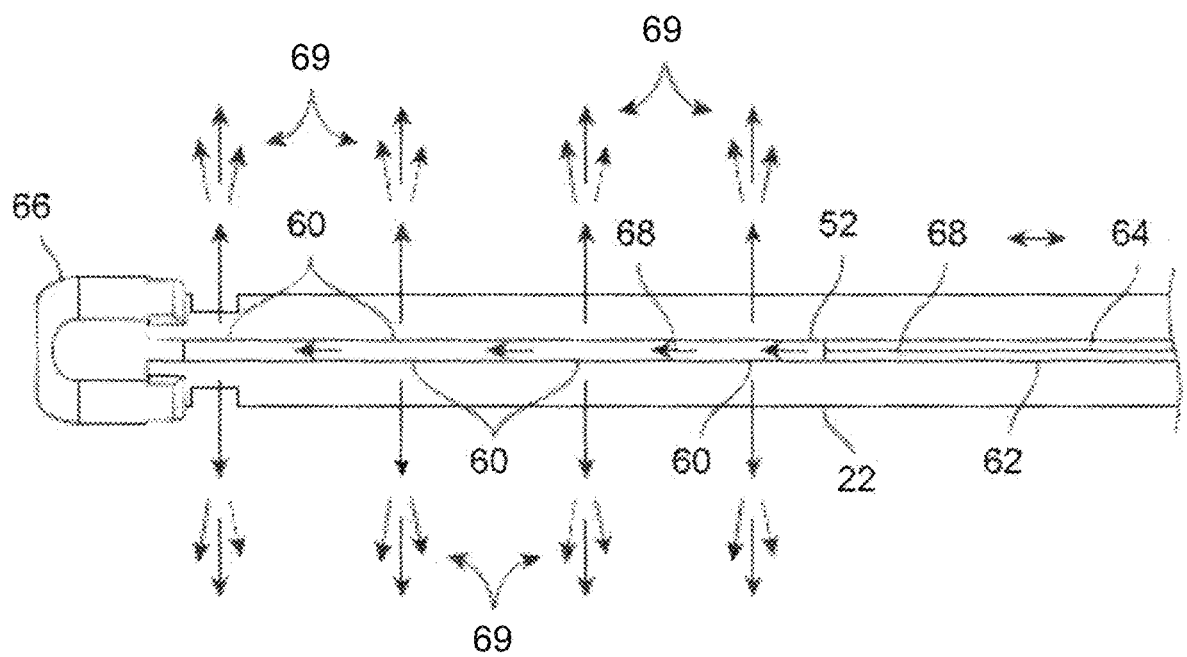

FIGS. 2A and 2B show cross-sectional side views of yet another variation of a cooling probe which utilizes a single infusion line in combination with a translatable delivery line. To accommodate various sizes and shapes of uterine cavities, the cooling probe may have a sliding adjustment that may be set, e.g., according to the measured length of the patient's uterine cavity. The adjustment may move along the sheath along the exhaust tube as well as the delivery line within the infusion line. The sheath may constrain the liner 20 and also control its deployment within the cavity.

In this variation, an infusion line 52 (as described above) may pass from the handle assembly and along or within the sheath and into the interior of liner 20. The infusion line 52 may be aligned along the probe 22 such that the infusion line 52 is parallel with a longitudinal axis of the probe 22 and extends towards the distal tip 66 of the probe 22. Moreover, the infusion line 52 may be positioned along the probe 22 such that the line 52 remains exposed to the corners of the liner 20 which extend towards the cornua. With the infusion line 52 positioned accordingly, the length of the line 52 within the liner 20 may have multiple openings formed along its length which act as delivery ports for the infused cryoablative fluid or gas. A separate translating delivery line 64, e.g., formed of a Nitinol tube defining an infusion lumen therethrough, may be slidably positioned through the length of the infusion line 52 such that the delivery line 64 may be moved (as indicated by the arrows in FIG. 2A) relative to the infusion line 52 which remains stationary relative to the probe 22.

The openings along the length of the infusion line 52 may be positioned such that the openings are exposed to the sides of the interior of the liner 20, e.g., cross-drilled. As the cryoablative fluid or gas is introduced through the delivery line 64, the infused cryoablative fluid or gas 68 may pass through the infusion line 52 and then out through the openings defined along the infusion line 52. By adjusting the translational position of the delivery line 64, the delivery line 64 may also cover a selected number of the openings resulting in a number of open delivery ports 60 as well as closed delivery ports 62 which are obstructed by the delivery line 64 position relative to the infusion line 52, as shown in the top view of FIG. 2B.

By translating the delivery line 64 accordingly, the number of open delivery ports 60 and closed delivery ports 62 may be adjusted depending on the desired treatment length and further ensures that only desired regions of the uterine tissue are exposed to the infused cryoablative fluid or gas 68. Once the number of open delivery ports 60 has been suitably selected, the infused cryoablative fluid or gas 68 may bypass the closed delivery ports 62 obstructed by the delivery line 64 and the fluid or gas may then be forced out through the open delivery ports 60 in a transverse direction as indicated by the infusion spray direction 69. The terminal end of the infusion line 52 may be obstructed to prevent the distal release of the infused fluid or gas 68 from its distal end. Although in other variations, the terminal end of the infusion line 52 may be left unobstructed and opened.

Figure 3A:
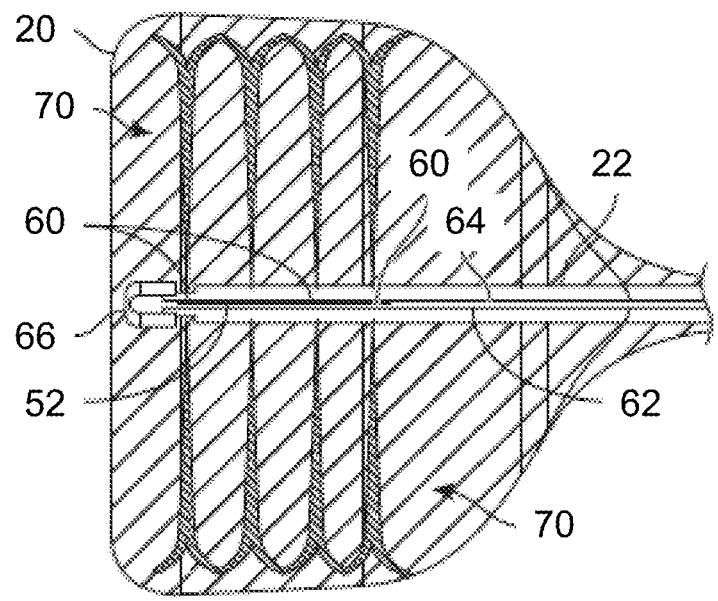
FIGS. 3A and 3B show top and perspective views of the expanded liner with four pairs of the open delivery ports exposed in apposed direction.
Figure 3B:
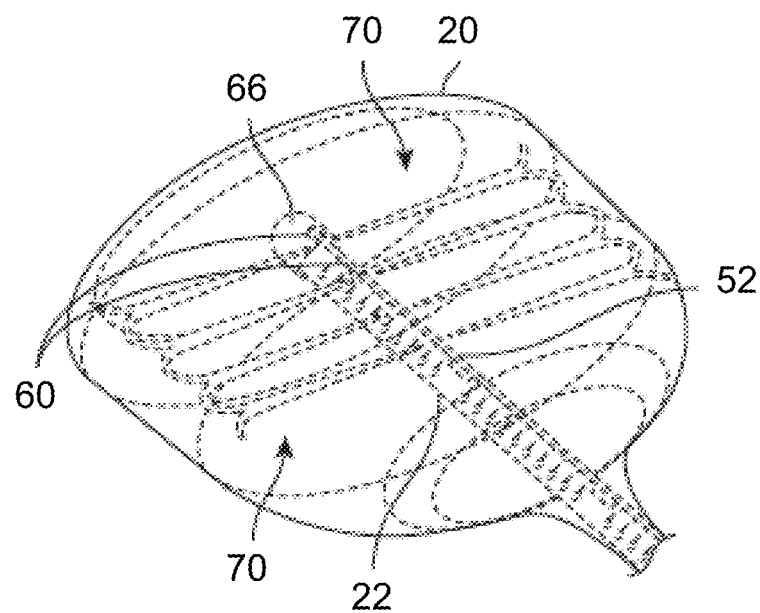

FIGS. 3A and 3B show top and perspective views of the expanded liner 20 with four pairs of the open delivery ports 60 exposed in apposed direction. Because the infused fluid or gas 68 may be injected into the liner 20, e.g., as a liquid, under relatively high pressure, the injected cryoablative liquid may be sprayed through the open delivery ports 60 in a transverse or perpendicular direction relative to the cooling probe 22. The laterally infused cryoablative fluid 70 may spray against the interior of the liner 20 (which is contacted against the surrounding tissue surface) such that the cryoablative liquid 70 coats the interior walls of the liner 20 due to turbulent flow causing heavy mixing. As the cryoablative liquid 70 coats the liner surface, the sprayed liquid 70 may absorb heat from the tissue walls causing rapid cooling of the tissue while also evaporating the liquid cryogen to a gas form that flows out through the cooling probe 22. This rapid cooling and evaporation of the cryoablative liquid 70 facilitates the creation of a fast and deep ablation over the tissue. During treatment, the temperature within the cavity typically drops, e.g., −86° C., within 2-3 seconds after the procedure has started. While the interior walls of the liner 20 are first coated with the cryoablative liquid 70, a portion of the cryoablative liquid 70 may no longer change phase as the procedure progresses.

While four pairs of the open delivery ports 60 are shown, the number of exposed openings may be adjusted to fewer than four pairs or more than four pairs depending on the positioning of the delivery line 64 and also the number of openings defined along the infusion line 52 as well as the spacing between the openings. Moreover, the positioning of the openings may also be adjusted such that the sprayed liquid 70 may spray in alternative directions rather than laterally as shown. Additionally and/or alternatively, additional openings may be defined along other regions of the infusion line 52.

Further variations of the treatment assembly features and methods which may be utilized in combination with any of the features and methods described herein may be found in the following U.S. Pat. Nos. 9,283,022; 9,486,267; 9,498,274; 9,445,860; 9,492,217; 9,510,887; 9,517,100; 9,492,218; 9,408,657; 8,858,543; 9,277,952; and 9,603,650. They may also be found in the following U.S. patent application Ser. No. 14/029,641 filed Sep. 17, 2013 (U.S. Pub. 2015/0080869); Ser. No. 14/019,928 filed Sep. 6, 2013 (U.S. Pub. 2014/005648); Ser. No. 14/265,799 (U.S. Pub. 2015/0289920); and Ser. No. 15/065,684 (U.S. Pub. 2016/0183999).

Each of the patent applications above is incorporated herein by reference in its entirety and for any purpose herein.

Figure 4A:
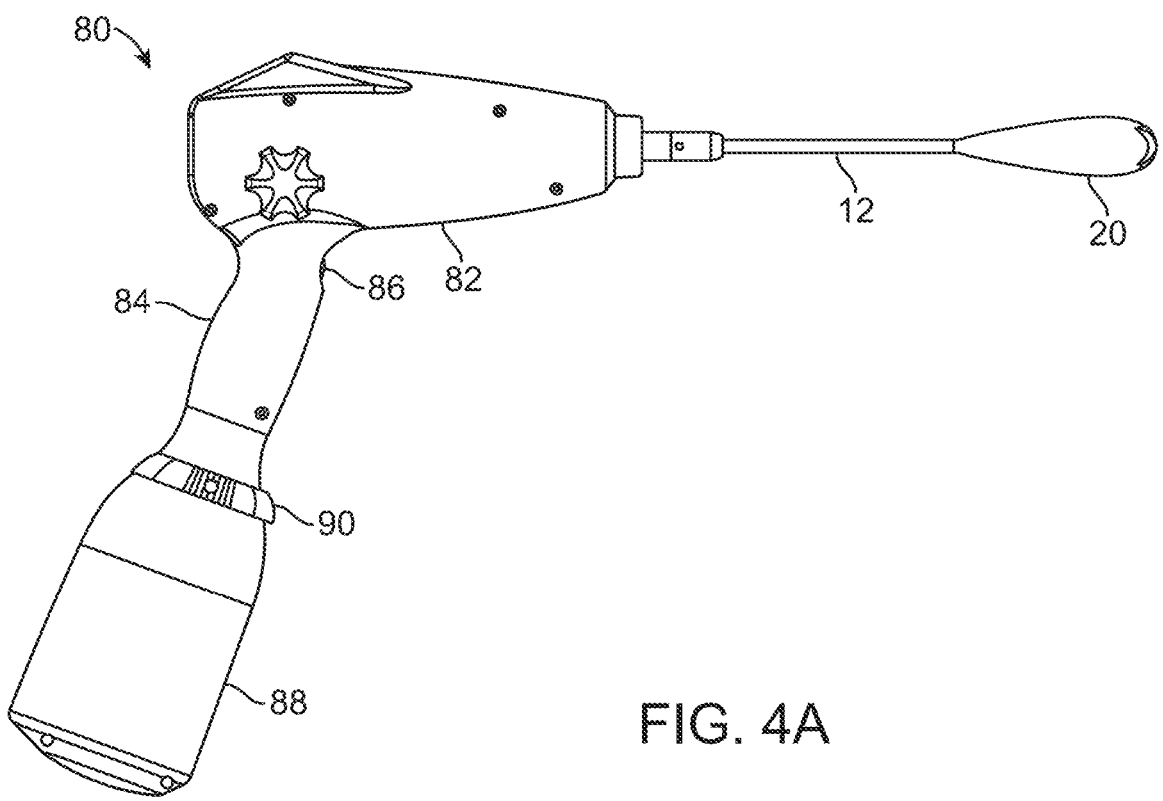
FIGS. 4A to 4C show side and assembly views of another variation of the treatment assembly.
Figure 4B:
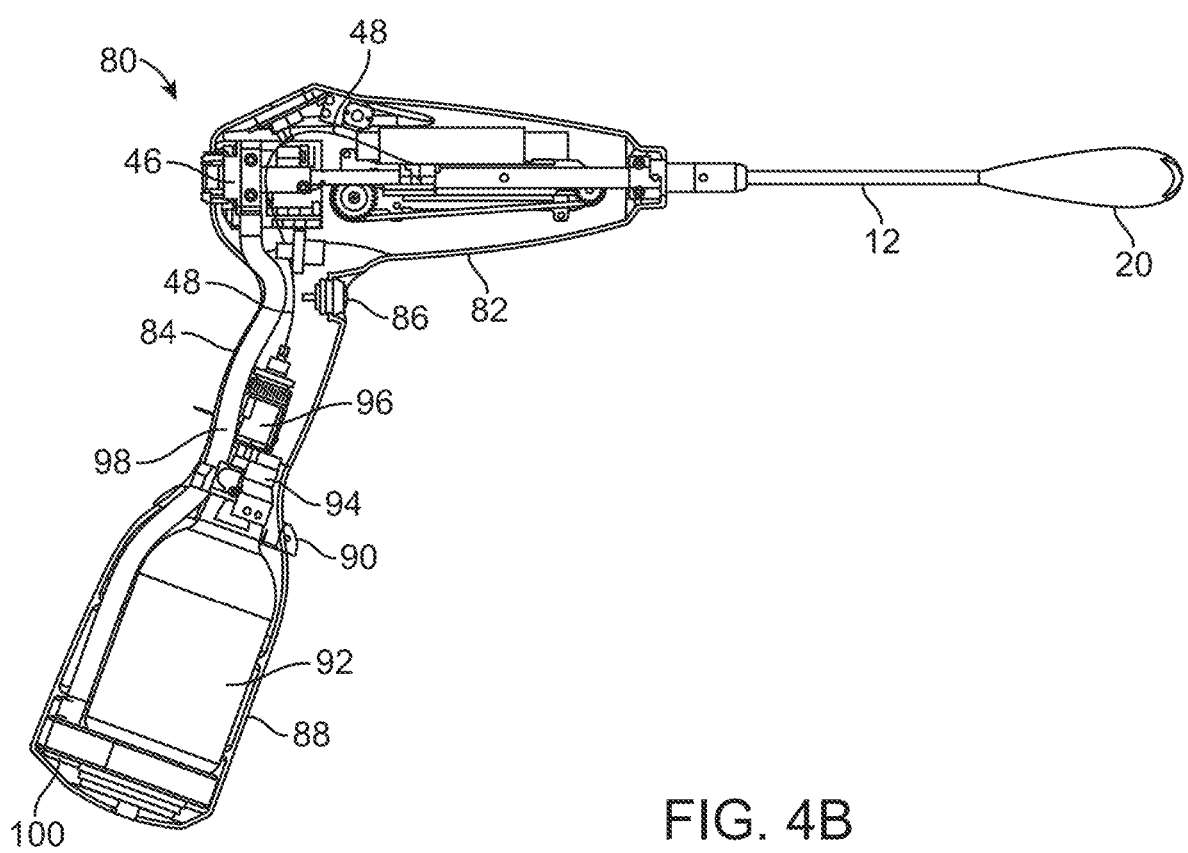
Figure 4C:
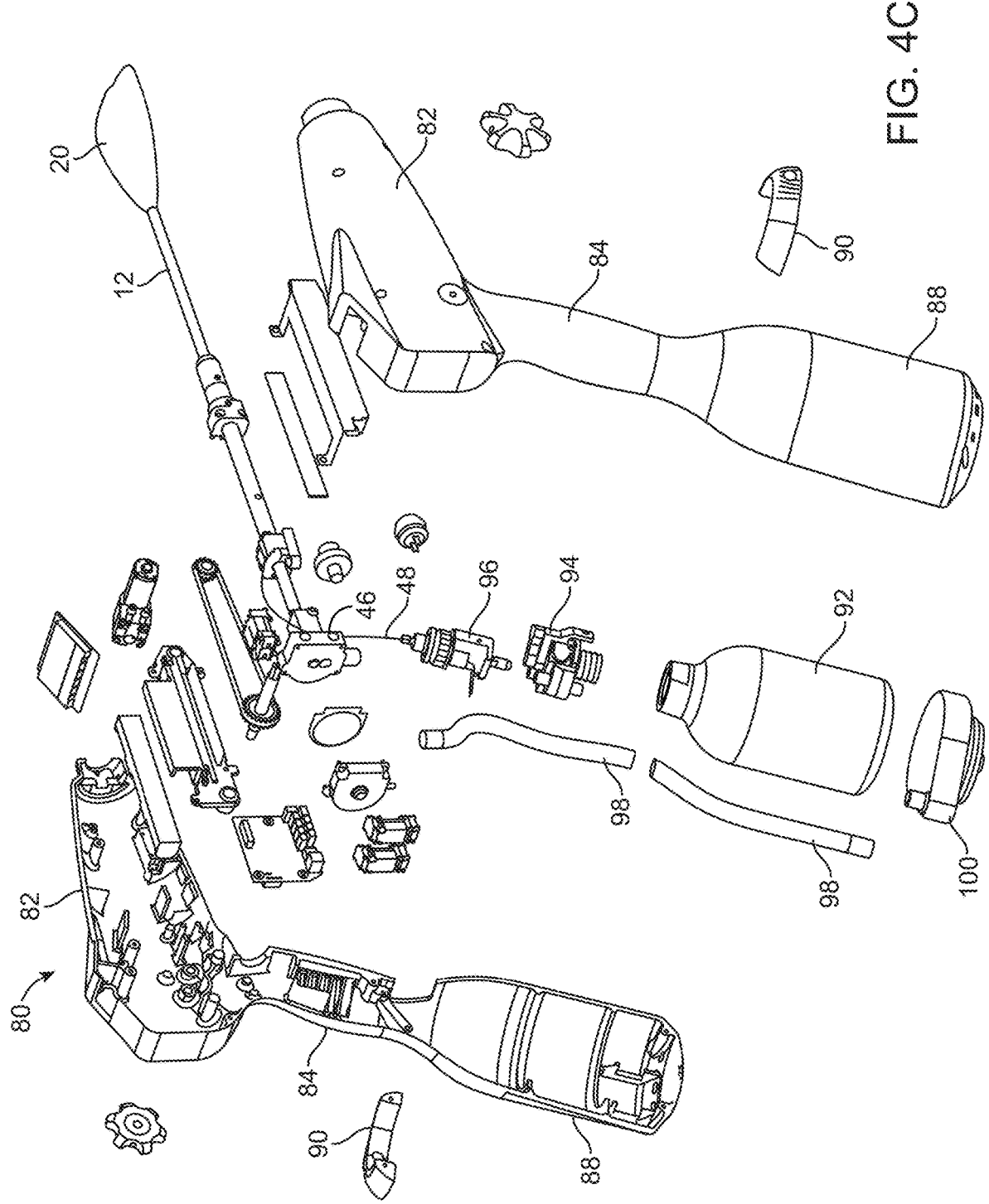

Yet another variation of the treatment assembly 80 is shown in the side and partial cross-sectional side views of FIGS. 4A and 4B which illustrate a housing 82 having a handle 84 and a reservoir housing 88 extending from and attached directly to the handle 84. FIG. 4C further illustrates a perspective assembly view of the treatment assembly 80 and some of its components contained internally.

The sheath 12 having the liner 20 may extend from the housing 82 while an actuator 86 may be located, for instance, along the handle 84 to enable the operator to initiate the cryoablative treatment. A reservoir or canister 92 fully containing the cryoablative agent (as described herein) may be inserted and retained within the reservoir housing 88. The reservoir housing 88 and/or the handle 84 may further incorporate a reservoir engagement control 90 which may be actuated, e.g., by rotating the control 90 relative to the handle 84, to initially open fluid communication with the reservoir or canister 92 to charge the system for treatment.

The reservoir or canister 92 may be inserted into the reservoir housing 88 and into secure engagement with a reservoir or canister valve 94 which may be coupled to the reservoir engagement control 90. The valve 94 may be adjusted to open the reservoir or canister 92 for treatment or for venting of the discharged cryoablative agent during or after treatment. An inflow modulation control unit 96 (e.g., an actuatable solenoid mechanism) may be coupled directly to the reservoir or canister valve 94 and the cryoablative fluid line 48 may be coupled directly to the modulation control unit 96 and through the sheath 12 and into fluid communication within the liner 20, as described herein.

During or after treatment, the discharged cryoablative fluid may be evacuated through the exhaust block 46 contained within the housing and then through the exhaust line 98 coupled to the exhaust block 46. The exhaust line 98 may extend through the handle 84 and the reservoir housing 88 and terminate at an exhaust line opening 100 which may be attached to another exhaust collection line, as further described herein.

Figure 5A:
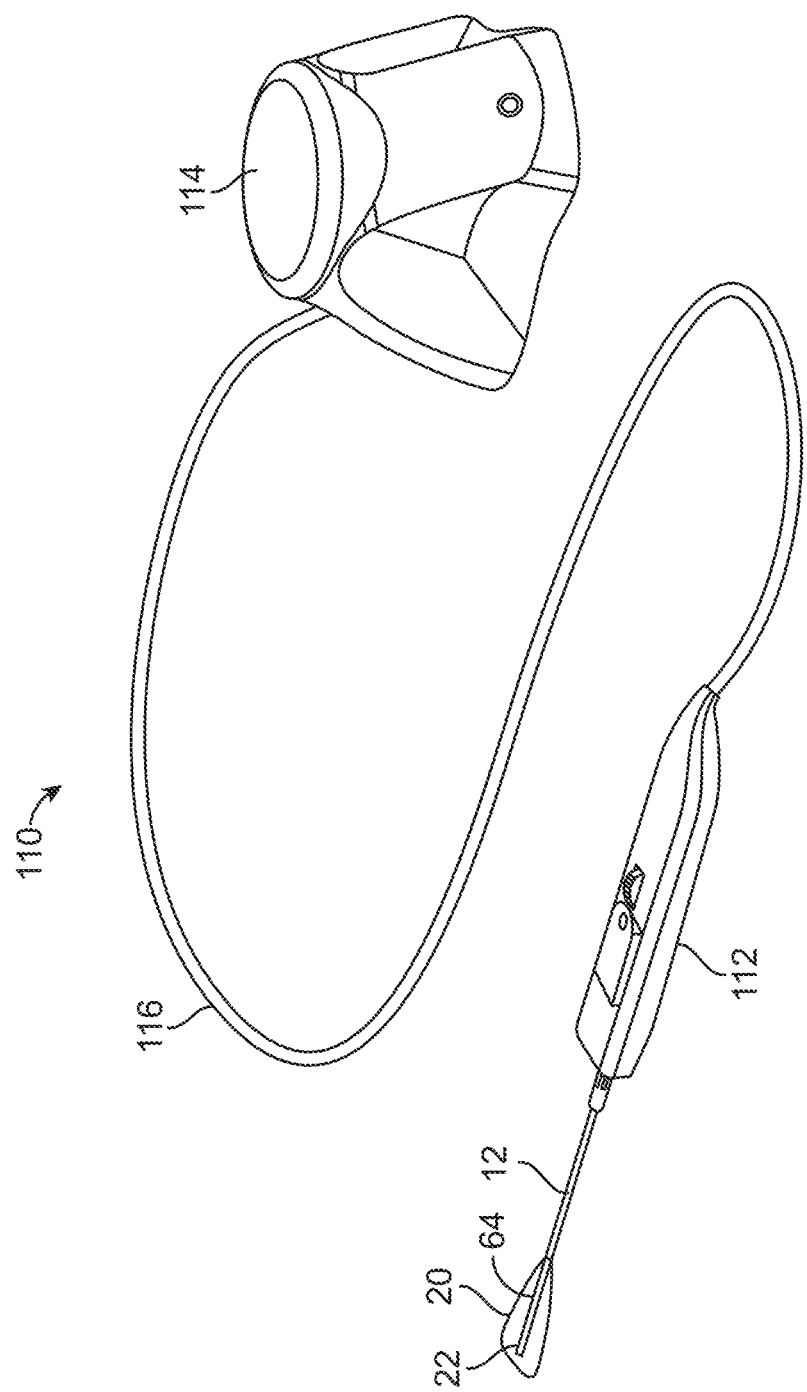
FIG. 5A shows one variation of a tethered system having a hand piece separated from a base station.

In yet another variation, the reservoir housing 88 and the electronics may be detached entirely from the sheath 12 and liner 20 assembly such that the treatment assembly is formed as a two-part or multi-component system which may be tethered or otherwise connected to one another. One example is illustrated in the perspective assembly view of FIG. 5A which shows a tethered system 110 having a hand piece 112 which may incorporate the sheath 12 and cooling probe 22 having the delivery line 64 surrounded by the liner 20, as described above. However, rather than incorporating the reservoir housing 88 and controller, the hand piece 112 may be separated from a base station 114 which incorporates the reservoir and controller, as described in further detail below. A flexible connection 116 may attach the hand piece 112 with the base station 114 where the hand piece 112 may either be permanently coupled to the base station 114 via the connection 116 or where the hand piece 112 may be detachable from the connection 116 and/or from the base station 114.

Figure 5B:
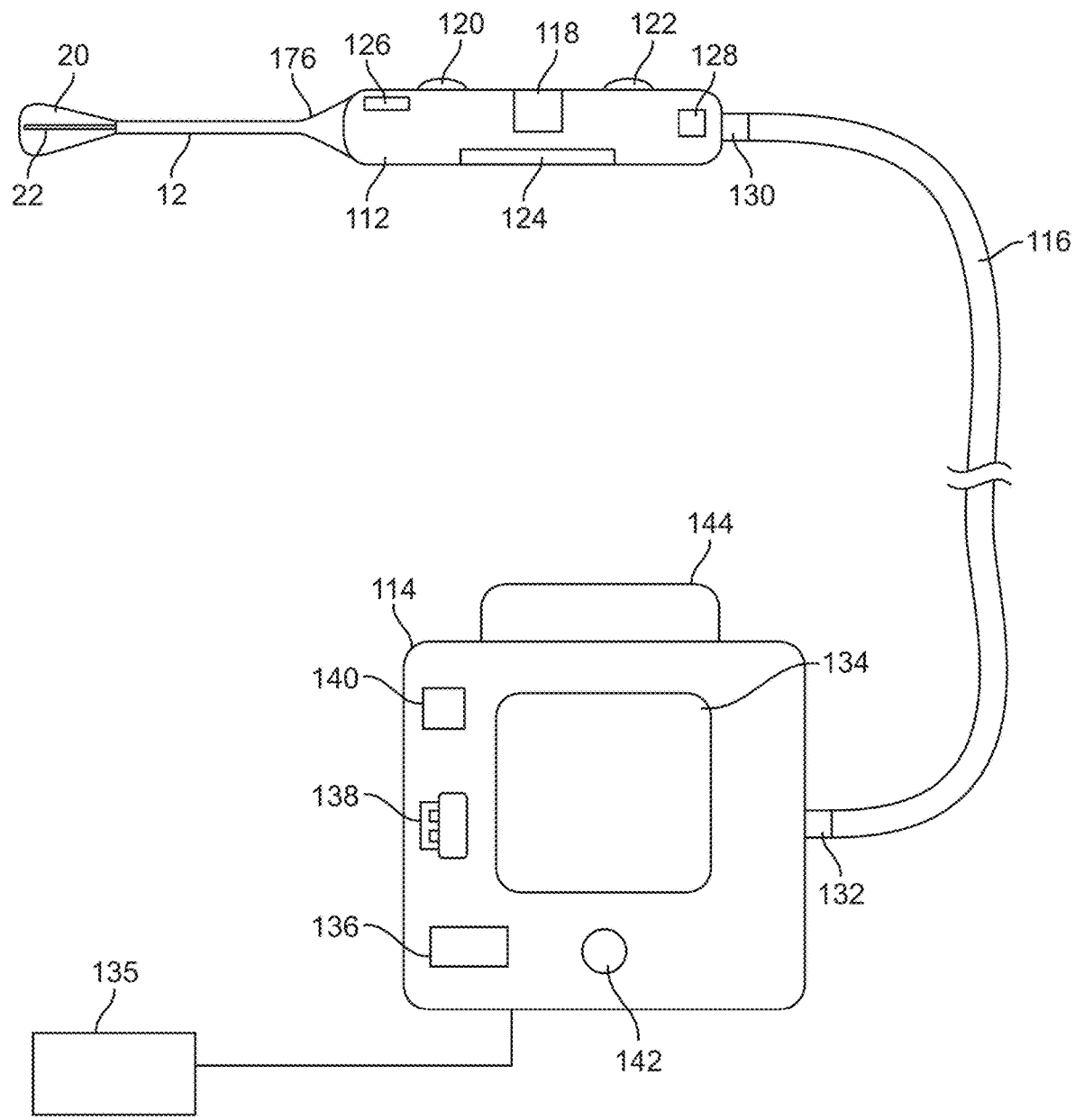
FIG. 5B shows a representative assembly view of the tethered treatment assembly having various components.

FIG. 5B illustrates a representative assembly view of the tethered treatment assembly having various components and further shows in one variation how the hand piece 112 and base station 114 may be separately configured. The hand piece 112 may optionally incorporate a display 118, e.g., LCD display, which shows various treatment parameters or indicators of the assembly. A control 120, e.g., thumbwheel, slide, etc., may also be incorporated for controlling functions such as positioning of the sheath 12 and/or probe 22 or other function. One or more actuators 122, e.g., button, switch, etc., may be incorporated as well for controlling functions such as infusing the cryoablative fluid into the liner 20 or exhausting the fluid from the liner 20.

Other mechanisms such as a potentiometer 124, e.g., linear potentiometer, may be incorporated for detecting and/or monitoring the position of the sheath 12 relative to the hand piece 112 housing. A pressure sensor 126 may also be incorporated for detecting and/or monitoring the pressure within the liner 20 prior to, during, and/or after a treatment. Additionally, an inflow control 128, e.g., inflow solenoid, may be incorporated into the hand piece 112 for controlling the inflow of the cryoablative fluid into the hand piece 112 from the base station 114.

While the hand piece 112 may be detachable from the base station 114 and/or connection 116, an infusion attachment 168 including, e.g., sheath 12, liner 20, and cooling probe 22, may also be removable and/or replaceable from the rest of the hand piece 112 allowing for the replacement of the infusion attachment 168 while reusing the hand piece 112. The hand piece 112 may be maintained at a treatment location for sterilization while the infusion attachment 168 may be disposed, refurbished, or repurposed on-site or at another location.

The connection 116 may be coupled to the hand piece 112 via a releasable connector 130, e.g., quick-connect mechanism, and it may be coupled to the base station 114 also via a second releasable connector 132, e.g., quick-connect mechanism. Connection 116 may enable the connection between the hand piece 112 and base station 114 to allow for the passage of various fluids and signals such as the cryoablation fluid, high pressure gas, electrical signals, pneumatic signals, etc. while remaining flexible enough so that the hand piece 112 may be moved and adjusted relative to the patient independently of the base station 114 which may remain in a stationary position relative to the patient.

The base station 114 has a housing which may include a display 134, e.g., LCD touchscreen, etc., for enabling interaction with or the display of parameters, messages, or warnings to the practitioner. A disposable sterile cover, e.g., transparent cover, may be optionally provided for placement upon or over the display 134 or the entire base station 114 so that the practitioner may interact with the display 134 during a procedure while maintaining sterility of the base station 114. Additionally and/or alternatively in other variations, a foot pedal 135 may be coupled to the base station 114 to provide a user interface to the practitioner for interacting with the base station 114.

A programmable microcontroller 136 may be integrated within the base station 114 and is in electrical communication with the hand piece 112 either through the connection 116 or wirelessly to control the treatment parameters as well as to receive and process signals from the hand piece 112 such as pressure readings, sheath positioning, etc. or any number of other signals. The microcontroller 136 may also control the various parameters within the base station 114 as well.

The base station 114 may also incorporate a pump 140 which may be fluidly coupled to the hand piece 112 and used to draw the spent exhaust from the interior of the liner 20, through the hand piece 112 and connection 116, and then through the base station 114 to, e.g., an exhaust collection assembly. A pneumatics controller 138, which may also include a pump, may be incorporated into the base station 114 and may be in fluid communication with the liner 20 for controlling the infusion or withdrawal of air within the liner 20, e.g., when monitoring the liner 20 for leaks or for initially expanding the liner 20 within the patient body. At least one actuator 142, e.g., button, may also be integrated for initiating treatment steps or facilitating control of the base station 114 during treatment. A reservoir assembly 144 may also be included within the base station 114 but may be removable from the base station 114, as described in further detail below.

Turning now to the hand piece 112, FIG. 6 shows a schematic view of one variation of the hand piece 112 where the infusion attachment 168, as mentioned above, may be removably coupled to a distal end of the housing of the hand piece via a coupling mechanism 178 which may secure the infusion attachment 168 for use but which may also decouple the infusion attachment 168 for replacement or disposal. The infusion attachment 168 may include a base 176 which couples to the housing of the hand piece 112 and which also supports components such as the insulating sheath 12 from which the liner 20 and cooling probe 22 extend. The infusion attachment 168 may also include the incorporate an inflow line 150 through which the cryoablative fluid 152 is infused into the liner interior and an exhaust line 156 through which the exhaust 158 is drawn from the liner interior. The base 176 may also optionally incorporate one or more lights 174, e.g., LED, for providing illumination as the device is inserted into the patient body.

Additionally and/or optionally, the sheath 12 may also incorporate one or more heating elements 175, e.g., strip heaters, along the length or a portion of the length of the sheath 12. The heating elements 175 may be positioned along an outer surface of the sheath 12 or within the sheath 12. During use, these heating elements 175 may be heated when the cryoablative fluid is delivered through the sheath 12 during a procedure and/or when the exhaust is evacuated from the liner 20 interior in order to prevent damage to tissue, e.g., cervix, contacting the sheath 12.

Because the heating elements 175 may draw its power from the base station 114 power supply 190 (or from a stationary outlet) which provides for a larger power source, the heating elements 175 may enable thermal protection for the contacted cervical tissue while potentially eliminating insulation for the sheath 12. This may result in a sheath 12 having a relatively smaller diameter which in turn may result in greater sheath 12 flexibility for increased comfort for the patient during device insertion, use, and removal.

Within the hand piece 112, its distal end may be configured to fluidly couple with the inflow line 150 and exhaust line 156 within the infusion attachment 168 when the two are coupled to one another. A valve 154, e.g., solenoid valve, may be in fluid communication with the inflow line 150 to provide control for metering the flow of cryoablative fluid into the liner 20 and a pressure sensor 162 may be in fluid communication with exhaust line 156 via pressure line 164 to enable monitoring of the pressure within the interior of the liner 20. An electrical line 166 may be connected to the pressure sensor 162 for transmitting electrical signals to and/or from the pressure sensor 162 to the microcontroller 136 located within the base station 114. Although the pressure sensor 162 may be housed within the hand piece 112 itself to ensure the fastest transmission of pressure readings within the liner 20, the pressure sensor may instead be housed externally of the hand piece 112 such as within the base station 114 or external to the system in which case the pressure sensor may communicate with the microcontroller wirelessly or via a wired connection.

Additionally, one or more control mechanisms such as control 170, e.g., thumbwheel, slide, etc., may be incorporated for controlling features such as deploying or retracting the sheath 12. Also, one or more actuators such as actuator 172, e.g., button, switch, etc., may be integrated for actuating any number of features or for providing various inputs into the device. A display 160, e.g., LCD display, for prompting and alerting the user through the treatment as well as for displaying any number of parameters to the user may also be integrated into the hand piece 112. The hand piece 112 may also incorporate one or more visual, auditory, or haptic mechanisms (e.g., LED, speaker, vibratory motor, etc.) to provide an alert to the user for any number of actions or alarms.

Although various electronics are illustrated within both the base station 114 and hand piece 112, other variations of the system may utilize the various electronics and/or components positioned entirely within the base station 114 or entirely within the hand piece 112. The components disposed within the base station 114 are not intended to be limiting and other variations of the system may incorporate any number of components within the hand piece 112 and base station 114.

The various connections for the hand piece 112 may be routed through connector 130, which is further illustrated respectively in the end and side views of FIGS. 7A and 7B.

As described herein, the connector 130 may be removably detached via a securement mechanism which not only mechanically attaches the hand piece 112 to the connector 116, but also seals and maintains the high pressure lines and low pressure pneumatic lines as well as maintains the electrical signals to and from the microcontroller. The end view shown in FIG. 7A illustrates one variation of how the individual lumens may be positioned relative to one another. As shown, the ablation agent lumen 180, exhaust lumen 182, and pneumatic lumen 184 may be disposed relative to one another and one or more electrical contacts and actuator lumens 186 may be aligned adjacent to one another.

Additionally and/or optionally, the connector 130 may have embedded electronics which are configured to identify the connection to either the appropriate hand piece 112 and/or base station 114 and verify that the connection was properly made using, e.g., proximity sensors, hall effects sensors, RFID chips, etc. The base station 114 and hand piece 112 may also incorporate embedded electronics to verify authenticity of the connected device or verify that the user is not attempting to re-use the device. For instance, both the hand piece 112, base station 114, and the base station reservoir 192 may utilize embedded or connected electronics such as RFID markers for tracking or identification purposes.

As described above, the reservoir assembly 144 is secured within the base station 114 and may be removed at the completion of treatment for refurbishing or disposal. The reservoir assembly 144 may contain not only the reservoir of the cryoablative fluid for the treatment procedure, but the assembly 144 may also incorporate a power supply or battery for providing power to the base station 114 and hand piece 112 as well. Moreover, the assembly 144 may also optionally incorporate any number of additional components as well.

The entire system, including the base station 114, may be used in a sterile condition or maintained within a sterile field during a procedure while the reservoir 192 and/or electronics may be removed for refurbishment and reuse after the completion of a procedure. Because the system is provided as several components, the reservoir 192 and/or electronics may be alternatively provided in a non-sterile condition for use in the base station 114 which may be maintained in a sterile condition. In yet another alternative, the base station 114, including the reservoir 192 and/or electronics, may be maintained outside of the sterile field while the hand piece 112 and connector 116 are maintained within the sterile field during a procedure.

Figure 8:
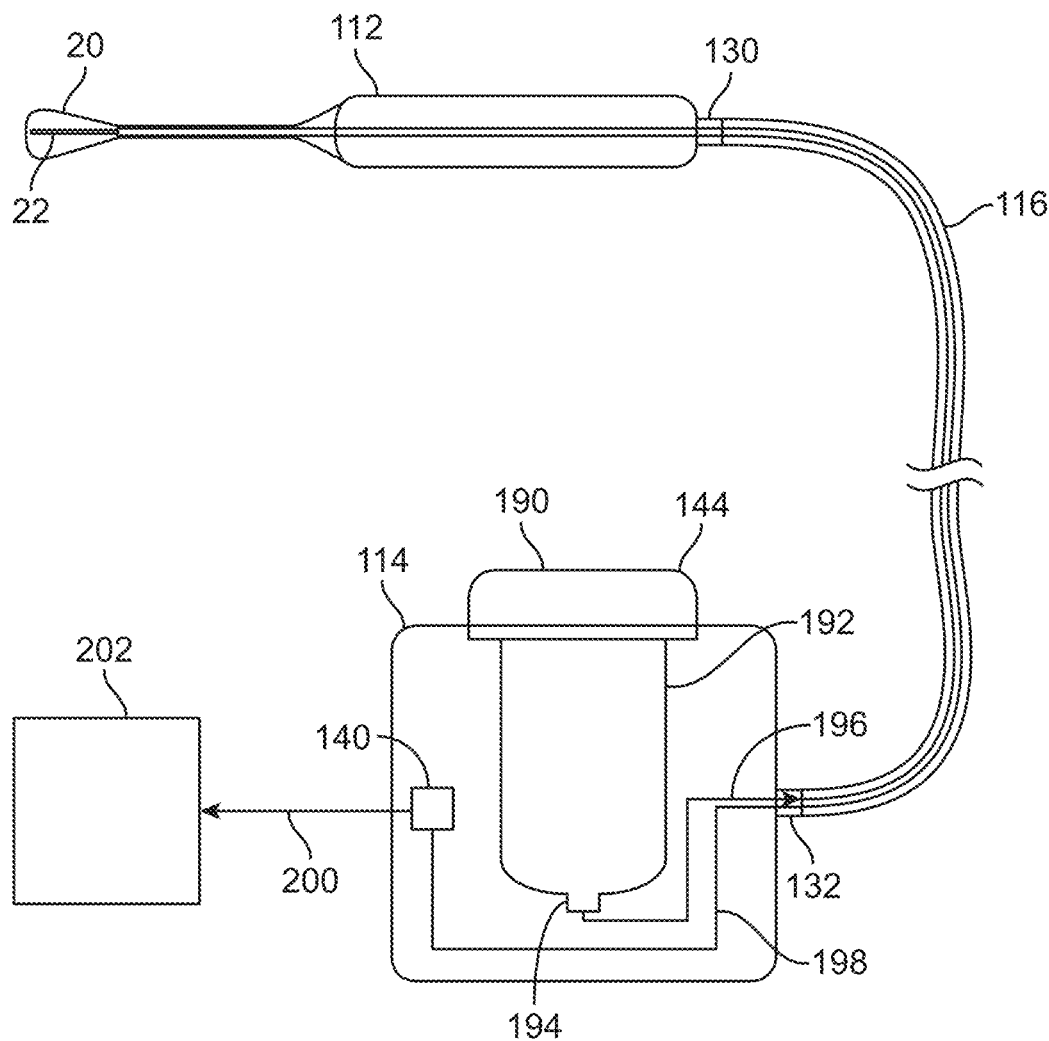
FIG. 8 shows a schematic view of one variation illustrating how the reservoir assembly may provide the cryoablative fluid once secured to the base station.

FIG. 8 shows a schematic view of one variation illustrating how the reservoir assembly 144 may provide the cryoablative fluid once secured to the base station 114. The assembly 144 may incorporate the power supply 190, as shown, while the reservoir 192 contains the cryoablative fluid within. Once secured to the base station 114, a port 194 may be aligned within a receiving channel within the base station 114 to engage with a base fluid lumen 196 leading from the port 194 to the base connector 132 to and the hand piece 112. A base exhaust lumen 198 may also extend within the base station 114 from the base connector 132 while urged via pump 140 through an exhaust lumen 200 for deposition or infusion within an exhaust reservoir 202 which may be separated from the base station 114 and connected via the exhaust lumen 200. Alternatively, the exhaust from exhaust lumen 198 may be vented to the environment instead. In the event that a separate exhaust reservoir 202 is used, such an exhaust reservoir may take the form of an expandable liner, bag, or other container. Examples of exhaust reservoirs which may be used with the devices disclosed herein are described in further detail in U.S. patent application Ser. No. 15/288,766 filed Oct. 7, 2016, which is incorporated herein by reference in its entirety and for any purpose.

In other variations, the exhaust reservoir 202 may be integrated within the base station 114 or fluidly coupled externally of the base station 114. The exhaust reservoir 202 may be comprised of a pressurized container, such as a bottle, which receives the exhaust and is then pressurized by the pump 140 within the exhaust reservoir 202. The pressurized container may be disengaged from the pump 140 for disposing the pressurized exhaust contained within and then reattached later.

By having the exhaust reservoir 202 and pump 140 separated from the hand piece 112, the back pressure in the hand piece 112 may be isolated from the external environment. For instance, a user may connect the scavenging suction from pump 140 to the exhaust port on the base station 114 and any pressure or vacuum drawn on the base station 114 from the vacuum may be isolated so as to not impact the hand piece 112 and distal end pressure.

Figure 9:
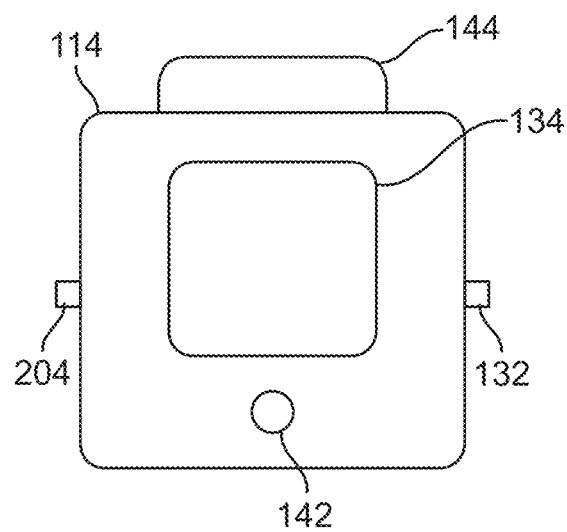
FIG. 9 illustrates a schematic view of an example of how the base station may incorporate a releasable connector for attachment of the base station to an external exhaust reservoir.

FIG. 9 illustrates a schematic view of an example of how the base station 114 may incorporate a releasable connector 204, e.g., quick-connect mechanism, for attachment of the base station 114 to an external exhaust reservoir 202. Also shown are the display 134, actuator 142, and reservoir assembly 144, as described above.

Figure 10:
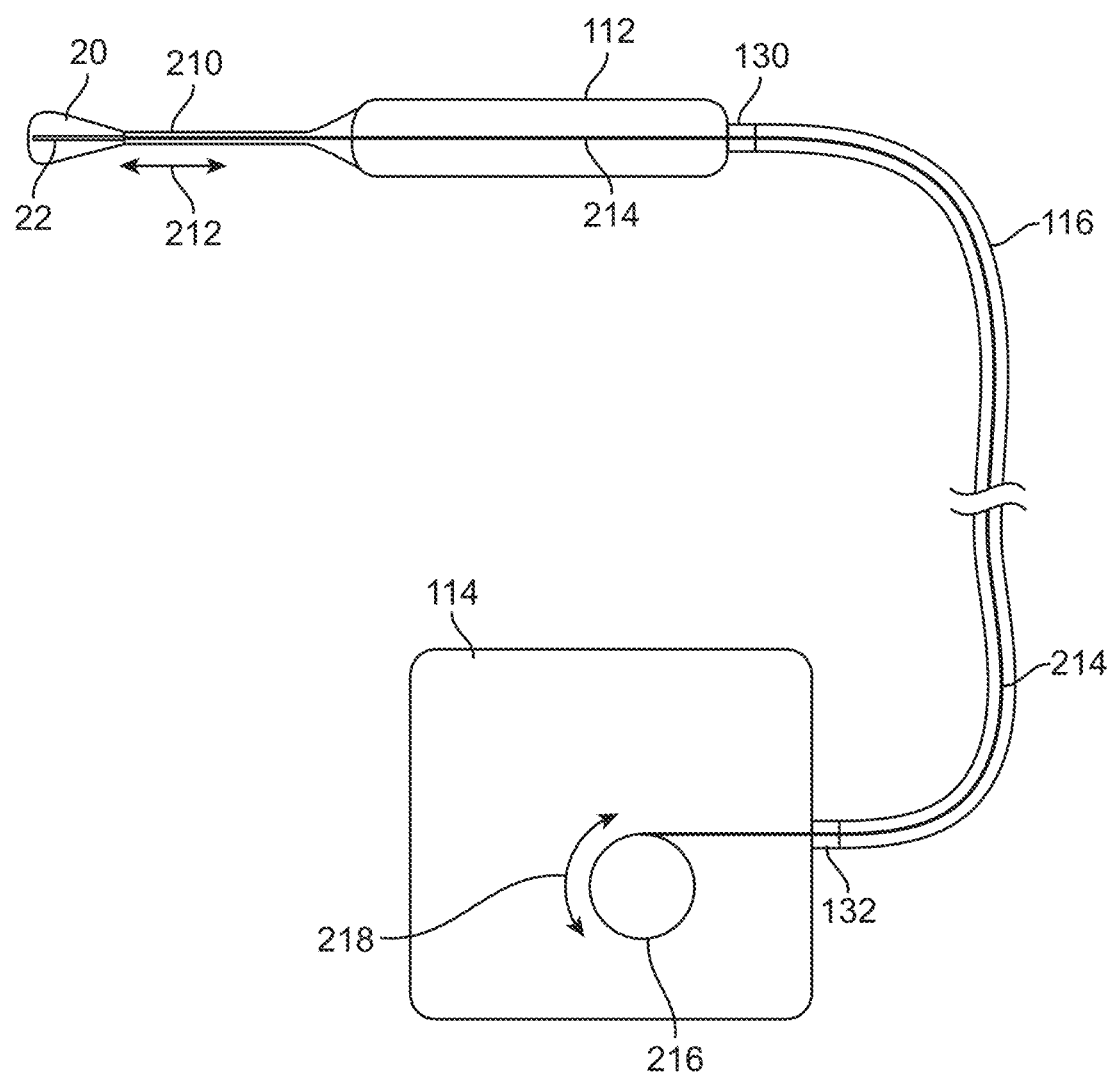
FIG. 10 shows a schematic view of the flexible connection incorporating an actuator cable capable of transmitting a linear movement through the connector and to the hand piece.

Aside from the transfer of fluids between the base station 114 and hand piece 112, the flexible connection 116 may also incorporate an actuator cable 214, e.g., cable, wire, or any structural element which is capable of transmitting a linear movement through the connector 116 and to the hand piece 112, as shown in the schematic view of FIG. 10. The actuator cable 214 may transmit a linear movement to the same actuator cable 214 or a separate cable within the hand piece 112 which may be coupled to the sheath 210. The actuator cable 214 can be coupled to the hand piece 112 via connector 130 and/or to the base station 114 via connector 132. Once coupled to the base station 114 and hand piece 112, the actuator cable 214 may be translated, e.g., in the direction of actuation 218, via a motor 216 such that the linear movement of the actuator cable 214 is transmitted through the connector 116, hand piece 112, and to the sheath 210 so that the sheath 210 and/or delivery line 64 may be moved distally or proximally as indicated by the longitudinal translation 212 during use in a procedure to not only translate the sheath 210 but to also cover a selected number of the openings resulting in a number of open delivery ports 60, as described herein.

Figure 11A:
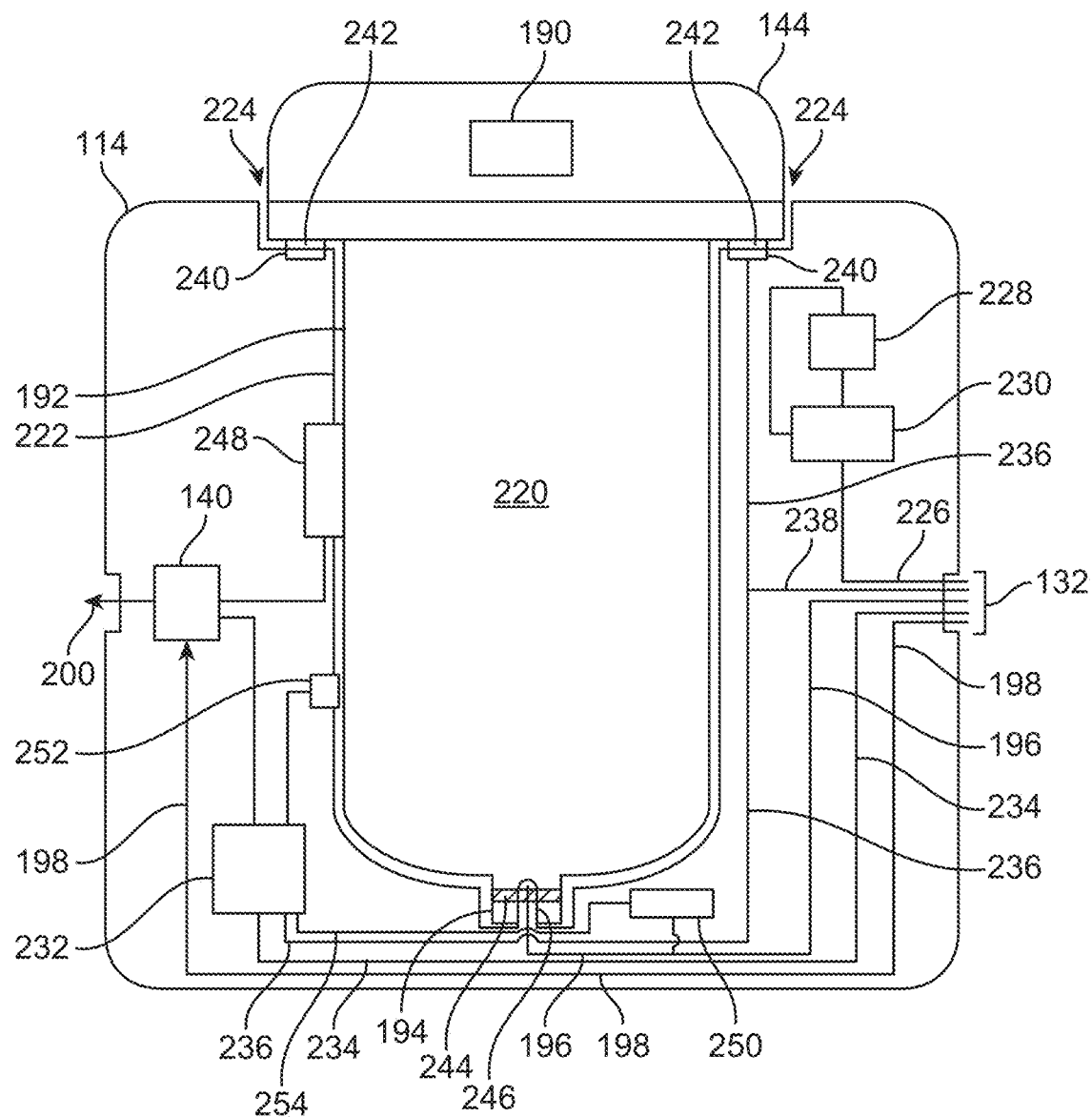
FIG. 11A shows a schematic view of some of the components which may be incorporated within a housing of the base station.

Turning back to the base station 114, FIG. 11A shows a schematic view of some of the components which may be incorporated within a housing. The reservoir assembly 144, which may be removable from the housing of the base station 114, may incorporate the power supply 190, such as a battery, within an enclosure to which the reservoir 192 is connected and contains the cryoablative fluid 220 within. The reservoir 192 may have a port 194 extending or defined along the reservoir 192 as shown in this variation as extending from a bottom surface of the reservoir 192 when the reservoir assembly 144 is secured within the base station 114. Because the port 194 extends from a bottom surface of the reservoir 192, the cryoablative fluid 220 contained within may effectively flow out of the reservoir 192 thereby eliminating any need for a sipper tube or other lumen to extend into the interior of reservoir 192 and also ensures that the entire contents of the reservoir 192 may be emptied.

Figure 11B:
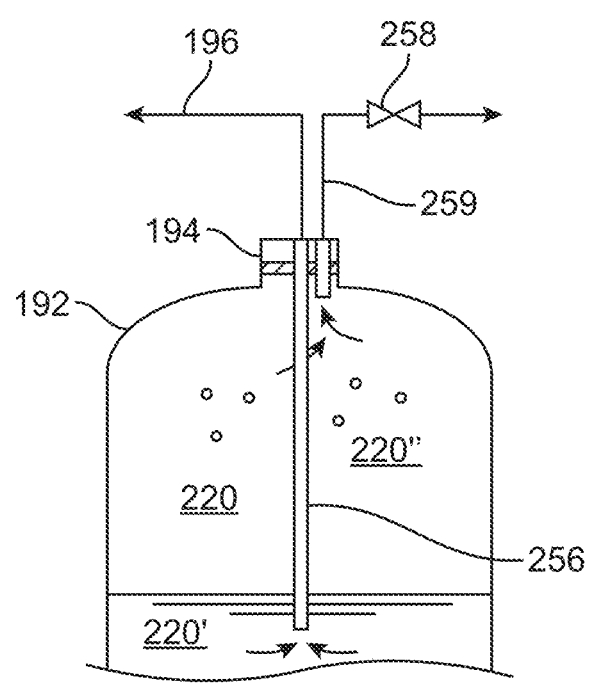
FIG. 11B shows a schematic side view of another variation of the reservoir using a sipper tube.

In the event that the reservoir 192 is oriented so that its port 194 extends from a top surface when secured within the base station 114, the reservoir 192 may be vented of excess fluid 220 by using a sipper tube 256 which extends into the interior of the reservoir 192, as shown in FIG. 11B. This variation of the reservoir 192 utilizing the sipper tube 256 may be used in combination with any of the features of the base station 114 or the system as described herein.

In the event that the reservoir 192 is used as a heat sink, the venting lumen 259 may be separate from the sipper tube 256. A valve 258, which is fluidly coupled to a venting lumen 259, may remain closed during use while fluid lumen 196 is opened. When fluid lumen 196 is closed, valve 258 may be opened in order to vent any gaseous cryoablative fluid 220". If the cryoablative fluid 220, is drawn up through the sipper tube 256 in liquid form 220', it will not extract the heat from the internal reservoir walls. (If the cryoablative fluid 220 were to convert into its gaseous form, heat from the internal reservoir walls would be extracted.) The gaseous form 220" of the cryoablative fluid 220 exiting from the separate venting lumen 259 through the port in the top of the reservoir 192 reduces the pressure within the reservoir 192 which will cause the liquid cryoablative fluid 220' at the bottom of the reservoir 192 to convert to a gaseous form 220" before exiting through the venting lumen 259 in the top of the reservoir 192. This liquid-to-gas phase change within the reservoir 192 will extract heat from the walls of the reservoir 192 causing the reservoir 192 temperature to drop and thereby using the reservoir 192 as a heat sink.

The cryoablative fluid 220 may be retained within the reservoir 192 by a seal 244 within the port 194 such that when the reservoir assembly 144 is secured within a reservoir assembly receiving channel 222 defined within the base station 114, a piercing manifold 246 extending within the receiving channel 222 is positioned to pierce the seal 244 and extend at least partially within the reservoir 192 in a sealed manner to enable the fluid within to flow into the manifold 246 and through the base fluid lumen 196 which extends through the base station 114 to the connection 132. In other variations, rather than utilizing a piercing manifold 246, the port receiving channel may instead be configured to open a valve into the reservoir 192 and the manifold 246 may be omitted. This variation may be utilized particularly if the reservoir 192 is to be reused.

A pressure sensor 250 may be optionally fluidly connected to base fluid lumen 196 so that the internal pressure from the fluid 220 within the reservoir 192 may be monitored by the microcontroller 232 which may be connected to the pressure sensor 250 via electrical connection 254. The pressure sensor 250 may also be configured as a mass sensor so that the pressure sensor 250 can be used to verify that the reservoir 192 is ready for treatment.

The microcontroller 232 may be electrically connected to not only to the components within the base station 114 but it may also communicate with the hand piece 112 and the various components within the hand piece 112 via one or more electrical connections 234 which may connect from the microcontroller 232 to the hand piece 112 via the connections 234 through the connection 116.

In other variations, rather than having a reservoir 192 be replaceable, the base station 114 may alternatively house a reservoir which is permanently integrated within the base station 114 such that the reservoir 192 is refillable by an external source. The base station 114 may have internal regulators and pressure switches to automate the process of filling the internal reservoir.

The base exhaust lumen 198 may also be seen extending from the connector 132 and through the base station 114 in fluid communication with the pump 140, which may also be in electrical communication with and controlled by the microcontroller 232, and through an exhaust lumen 200. A thermal mass/evaporator 248 connected to the pump 140 may be positioned within the receiving channel 222 of the base station 114 such that the thermal mass/evaporator 248 contacts the reservoir 192 directly in order to facilitate evaporation of any remaining liquid cryogen that is exhausted.

Additionally, the base station 114 may also include a pneumatic lumen 226 leading to the connector 132 and fluidly coupled to a pneumatic control 230 (e.g., solenoids, tubing, valves, etc.) and a pump 228 for providing the air (or other gas) which may be used for infusion into the liner 20 during a procedure. The pneumatic control 230 and/or pump 228 may also be electrically coupled to the microcontroller 232 for controlling the operation of the pneumatic control 230. The pneumatic lumen 226 and/or pump 228 may also optionally incorporate one or more heating elements which may be used to warm air being infused into the liner 20 in order to facilitate patient comfort and/or to facilitate removal of the device by thawing the frozen tissue contacted by the liner.

Additionally and/or optionally, the base station 114 may also integrate a temperature sensor 252 which is electrically coupled to the microcontroller 232 and positioned within the receiving channel 222 for contacting the reservoir 192. The temperature sensor 252 may be used to monitor the reservoir temperature and may also be configured with one or more heating elements which may be controlled by the microcontroller 232 to regulate the temperature of the reservoir 192 in order to maintain the system within optimal treatment parameters.

As the reservoir assembly 144 may be removable from the base station 114, the reservoir assembly 144 may be secured within the receiving channel 222 via any number of engagement mechanisms 224, e.g., threaded features or other mating features which help to ensure that the reservoir is fully seated and sealed within the receiving channel 222. Because the reservoir assembly 144 may contain the power supply 190 (although in other variations the power may be supplied to the base station 114 via an external power source, e.g., wall outlet, etc.), the housing of the assembly 144 may contain one or more electrical contacts 242 which may connect with or contact complementary electrical contacts 240 located on the base station 114. The electrical contacts 240 located on the base station 114 may be electrically coupled to the various components within the base station via a power supply connection 236 as well as to the hand piece through connection 116 via a power supply line 238. Hence, when the reservoir assembly 144 is fully seated within the base station 114, the power supply 190 may supply the requisite to the components within the base station 114 as well as the hand piece 112.

Figure 12:
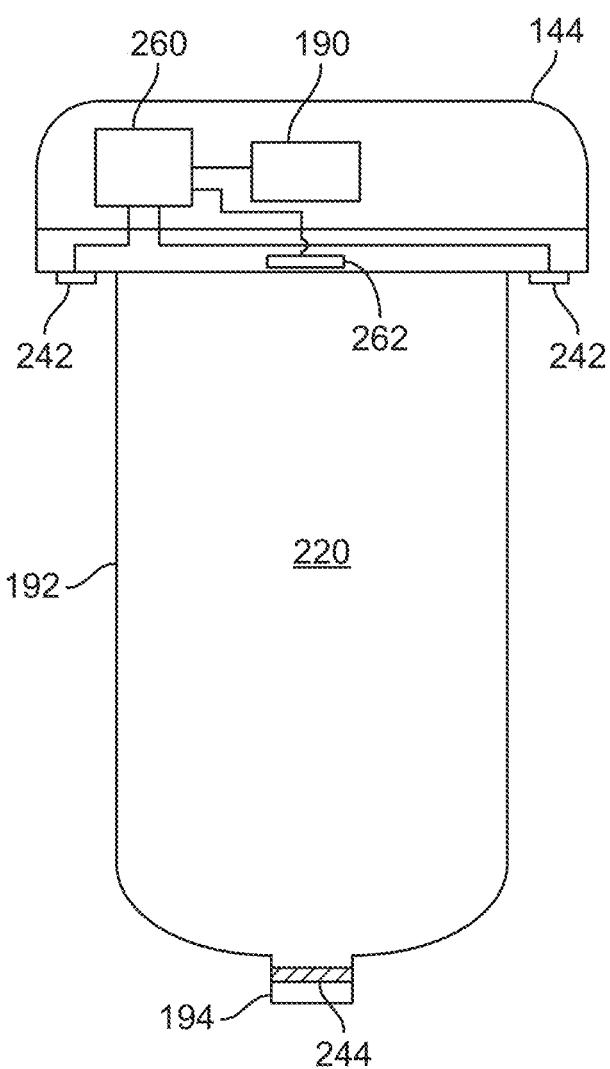
FIG. 12 shows a schematic view of the reservoir assembly removed from the base station.

The reservoir assembly 144 is shown in the schematic view of FIG. 12 removed from the base station 114. The reservoir 192, port 194, electrical contacts 242, and seal 244 are shown for clarity purposes. Because the reservoir assembly 144 may be removable from the base station 114, the base station 114 may have the microcontroller 232 programmable to detect or monitor for a mating sensor or electronics in the assembly 144 which can be used to verify whether the reservoir 192 is full or discharged, e.g., to prevent re-use of a partially empty reservoir 192. After the end of a treatment procedure, the reservoir assembly 144 may be removed from the base station 114 to allow for the insertion of a new reservoir assembly and the discharged reservoir assembly 144 may be either refurbished or disposed after use.

While the microcontroller 232 may be programmed to monitor the use of the reservoir assembly 144, the reservoir assembly 144 may also include a separate microcontroller 260 which may be electrically connected to a pressure sensor 262 for monitoring a pressure level of the fluid 220 within the reservoir 192 as well as being electrically connected to the power supply 190 for determining its charge level and to the contacts 242 for determining whether the power supply 190 has made sufficient contact with the base station contacts. Aside from monitoring pressure and power levels, the base microcontroller 260 may also be programmed to monitor various parameters of the reservoir assembly 144 such as current or historic temperature, humidity, power levels, etc.

Additionally, the microcontroller 260 may also be programmed to lock to the base station 114 after installation to prevent the detachment of a full or partially full reservoir assembly via optional interlocks which may be configured to deactivate after completion of a treatment and/or venting of the reservoir 192.

The volume of the reservoir 192 may also be varied depending on the desired amount of fluid 220 for treatment. For instance, the reservoir 192 may be configured to hold enough of the fluid 220 for a single treatment or for multiple treatments. Alternatively, the base station 114 may be integrated with a non-removable reservoir 192 so that the base station 114 may be interfaced or connected to a large external reservoir used to supply the fluid for treatment and/or to recharge the reservoir 192.

While illustrative examples are described above, it will be apparent to one skilled in the art that various changes and modifications may be made therein. Moreover, various apparatus or procedures described above are also intended to be utilized in combination with one another, as practicable. The appended claims are intended to cover all such changes and modifications that fall within the true spirit and scope of the invention.

What is claimed is:

1. A treatment system, comprising:
    an elongate probe having a distal tip and a flexible length, at least one infusion lumen positioned through or along the elongate probe;
    a handpiece having a detachable infusion attachment coupled to the elongate probe;
    a liner expandably surrounding and enclosing the distal tip of the probe such that a cryoablative fluid introduced through the probe is sprayed into contact with an interior surface of the liner and coats the interior surface;
    a base having a reservoir of the cryoablative fluid;
    a connection having an elongate flexible body, the connection having at least one fluid lumen for delivery of the cryoablative fluid from the reservoir and to the at least one infusion lumen; and
    a controller positioned within the base, wherein the controller is configured to monitor the cryoablative fluid.

2. The system of claim 1 wherein the reservoir is removably securable within the base, the reservoir further comprising a power supply configured for electrical communication with the controller when secured.

3. The system of claim 1 wherein the reservoir further comprises electrical contacts configured to electrically couple to the base.

4. The system of claim 1 wherein the reservoir contains a port, the port configured to release cryoablative fluid from the reservoir.

5. The system of claim 4 wherein the port comprises a seal.

6. The system of claim 5 further comprising a manifold, the manifold being configured to pierce the seal and provide a passageway for the cryoablative fluid to flow from the reservoir to the connection.

7. The system of claim 4 wherein the port further comprises a valve configured to provide a passageway for the cryoablative fluid to flow from the reservoir to the connection.

8. The system of claim 1 wherein the base further comprises a pressure sensor for monitoring the pressure of the fluid in the reservoir, the controller being electrically connected to the pressure sensor.

9. The system of claim 1 wherein the base further comprises a pump for providing fluid into the liner, the controller being electrically connected to the pump.

10. The system of claim 1 wherein the base further comprises an exhaust pump, the controller being electrically connected to the exhaust pump.

11. The system of claim 1 wherein the base further comprises a temperature sensor for monitoring temperature in the reservoir, the controller being electrically connected to the temperature sensor.

12. The system of claim 1 further comprising a second microcontroller within the base.

13. The system of claim 12 wherein the second microcontroller monitors pressure levels of the reservoir and power levels of the base.

14. A method of treating tissue, comprising:
   securing a reservoir assembly within a base, the reservoir assembly holding a cryoablative fluid;
   positioning an elongate probe having a distal tip and a flexible length, at least one infusion lumen positioned through or along the elongate probe, wherein the elongate probe is coupled to an infusion attachment which is detachable from a hand piece;
   expanding a liner surrounding and enclosing the distal tip of the probe such that a cryoablative fluid introduced through the probe is sprayed into contact with an interior surface of the liner and coats the interior surface;
   infusing the cryoablative fluid from the reservoir to the at least one infusion lumen through a connection having an elongate flexible body, the connection having at least one fluid lumen; and
   monitoring the cryoablative fluid with a controller positioned within the base.

15. The method of claim 14 wherein monitoring the cryoablative fluid comprises monitoring a pressure of the cryoablative fluid using a pressure sensor.

16. The method of claim 14 wherein securing a reservoir assembly comprises detachably securing the reservoir assembly to the base.

17. The method of claim 16 further comprising electrically connecting the reservoir assembly to the base using electrical contacts.

18. The method of claim 14 further comprising providing a seal at a port of the reservoir.

19. The method of claim 18 further comprising piercing the seal with a manifold, providing a passageway for the cryoablative fluid to flow from the reservoir to the connection.

20. The method of claim 14 further comprising placing a valve at a port of the reservoir, the valve configured to provide a passageway for the cryoablative fluid to flow from the reservoir to the connection.

* * * * *